(12) United States Patent
Waycuilis

(10) Patent No.: US 8,282,810 B2
(45) Date of Patent: Oct. 9, 2012

(54) BROMINE-BASED METHOD AND SYSTEM FOR CONVERTING GASEOUS ALKANES TO LIQUID HYDROCARBONS USING ELECTROLYSIS FOR BROMINE RECOVERY

(75) Inventor: John J. Waycuilis, Cypress, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 536 days.

(21) Appl. No.: 12/477,307

(22) Filed: Jun. 3, 2009

(65) Prior Publication Data

US 2009/0308759 A1  Dec. 17, 2009

Related U.S. Application Data

(60) Provisional application No. 61/061,475, filed on Jun. 13, 2008.

(51) Int. Cl.
*C25B 1/24* (2006.01)
*C07C 2/86* (2006.01)
*C07C 2/88* (2006.01)
*C07B 39/00* (2006.01)

(52) U.S. Cl. ......... 205/619; 585/733; 585/310; 585/943
(58) Field of Classification Search ........................ None
See application file for complete search history.

(56) References Cited

U.S. PATENT DOCUMENTS

| | | |
|---|---|---|
| 2,168,260 A | 8/1939 | Heisel et al. |
| 2,246,082 A | 6/1941 | Vaughan et al. |
| 2,320,257 A | 5/1943 | Beekhuis |
| 2,488,083 A | 11/1949 | Gorin et al. |
| 2,536,457 A | 1/1951 | Mugdan |
| 2,666,024 A | 1/1954 | Low et al. |
| 2,677,598 A | 5/1954 | Crummett et al. |
| 2,941,014 A | 6/1960 | Rothweiler et al. |
| 3,076,784 A | 2/1963 | Schulte-Huermann et al. |
| 3,172,915 A | 3/1965 | Borkowski et al. |
| 3,246,043 A | 4/1966 | Rosset et al. |
| 3,254,023 A | 5/1966 | Miale et al. |
| 3,273,964 A | 9/1966 | Rosset |
| 3,291,708 A * | 12/1966 | Juda .............................. 205/618 |
| 3,294,846 A | 12/1966 | Livak et al. |

(Continued)

FOREIGN PATENT DOCUMENTS

CA  1099656  4/1981

(Continued)

OTHER PUBLICATIONS

Wauters et al, "Electrolytic Membrane Recovery of Bromine from Waste Hydrogen Bromide Streams", AIChE Journal, vol. 44, No. 10, pp. 2144-2148, Oct. 1998.*

(Continued)

*Primary Examiner* — Harry D Wilkins, III
(74) *Attorney, Agent, or Firm* — Jack E. Ebel; Corey S. Tumey; Rodney F. Brown

(57) ABSTRACT

A variety of methods and systems are disclosed herein, including, in one embodiment, a method comprising: providing a stream comprising halogenated alkanes; forming synthesis products comprising hydrocarbons and hydrogen bromide from synthesis reactants comprising at least a portion of the halogenated alkanes; and recovering at least a portion of the bromine, the recovering comprising electrolysis.

30 Claims, 3 Drawing Sheets

U.S. PATENT DOCUMENTS

| | | |
|---|---|---|
| 3,310,380 A | 3/1967 | Lester |
| 3,314,762 A | 4/1967 | Hahn |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,615,265 A | 10/1971 | Gartner |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A * | 3/1980 | Coker et al. ............... 205/525 |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |

| Patent | Date | Inventor |
|---|---|---|
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,735,747 A | 4/1988 | Ollivier et al. |
| 4,737,594 A | 4/1988 | Olah |
| 4,748,013 A | 5/1988 | Saito et al. |
| 4,762,596 A * | 8/1988 | Huang et al. ............... 205/359 |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaeding |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |
| 5,233,113 A | 8/1993 | Periana et al. |
| 5,237,115 A | 8/1993 | Makovec et al. |
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |

| | | | | | | |
|---|---|---|---|---|---|---|
| 5,401,894 A | 3/1995 | Brasier et al. | | 5,928,488 A | 7/1999 | Newman |
| 5,406,017 A | 4/1995 | Withers, Jr. | | 5,952,538 A | 9/1999 | Vaughn et al. |
| 5,411,641 A * | 5/1995 | Trainham et al. ............. 205/618 | | 5,959,170 A | 9/1999 | Withers, Jr. et al. |
| 5,414,173 A | 5/1995 | Garces et al. | | 5,968,236 A | 10/1999 | Bassine |
| 5,430,210 A | 7/1995 | Grasselli et al. | | 5,969,195 A | 10/1999 | Stabel et al. |
| 5,430,214 A | 7/1995 | Smith et al. | | 5,977,402 A | 11/1999 | Sekiguchi et al. |
| 5,430,219 A | 7/1995 | Sanfilippo et al. | | 5,983,476 A | 11/1999 | Eshelman et al. |
| 5,433,828 A * | 7/1995 | van Velzen et al. ........... 205/619 | | 5,986,158 A | 11/1999 | Van Broekhoven et al. |
| 5,436,378 A | 7/1995 | Masini et al. | | 5,994,604 A | 11/1999 | Reagen et al. |
| 5,444,168 A | 8/1995 | Brown | | 5,998,679 A | 12/1999 | Miller |
| 5,446,234 A | 8/1995 | Casci et al. | | 5,998,686 A | 12/1999 | Clem et al. |
| 5,453,557 A | 9/1995 | Harley et al. | | 6,002,059 A | 12/1999 | Hellring et al. |
| 5,456,822 A | 10/1995 | Marcilly et al. | | 6,015,867 A | 1/2000 | Fushimi et al. |
| 5,457,255 A | 10/1995 | Kumata et al. | | 6,018,088 A | 1/2000 | Olah |
| 5,464,799 A | 11/1995 | Casci et al. | | 6,022,929 A | 2/2000 | Chen et al. |
| 5,465,699 A | 11/1995 | Voigt | | 6,034,288 A | 3/2000 | Scott et al. |
| 5,470,377 A | 11/1995 | Whitlock | | 6,056,804 A | 5/2000 | Keefer et al. |
| 5,480,629 A | 1/1996 | Thompson et al. | | 6,068,679 A | 5/2000 | Zheng |
| 5,486,627 A | 1/1996 | Quarderer, Jr. et al. | | 6,072,091 A | 6/2000 | Cosyns et al. |
| 5,489,719 A | 2/1996 | Le et al. | | 6,087,294 A | 7/2000 | Klabunde et al. |
| 5,489,727 A | 2/1996 | Randolph et al. | | 6,090,312 A | 7/2000 | Ziaka et al. |
| 5,500,297 A | 3/1996 | Thompson et al. | | 6,093,306 A | 7/2000 | Hanrahan et al. |
| 5,510,525 A | 4/1996 | Sen et al. | | 6,096,932 A | 8/2000 | Subramanian |
| 5,523,503 A | 6/1996 | Funk et al. | | 6,096,933 A | 8/2000 | Cheung et al. |
| 5,525,230 A | 6/1996 | Wrigley et al. | | 6,103,215 A | 8/2000 | Zones et al. |
| 5,538,540 A | 7/1996 | Whitlock | | 6,107,561 A | 8/2000 | Thompson |
| 5,563,313 A | 10/1996 | Chung et al. | | 6,117,371 A | 9/2000 | Mack |
| 5,565,092 A | 10/1996 | Pannell et al. | | 6,124,514 A | 9/2000 | Emmrich et al. |
| 5,565,616 A | 10/1996 | Li et al. | | 6,127,588 A | 10/2000 | Kimble et al. |
| 5,571,762 A | 11/1996 | Clerici et al. | | 6,130,260 A | 10/2000 | Hall et al. |
| 5,571,885 A | 11/1996 | Chung et al. | | 6,143,939 A | 11/2000 | Farcasiu et al. |
| 5,599,381 A | 2/1997 | Whitlock | | 6,169,218 B1 | 1/2001 | Hearn et al. |
| 5,600,043 A | 2/1997 | Johnston et al. | | 6,180,841 B1 | 1/2001 | Fatutto et al. |
| 5,600,045 A | 2/1997 | Van Der Aalst et al. | | 6,187,871 B1 | 2/2001 | Thompson et al. |
| 5,609,654 A | 3/1997 | Le et al. | | 6,187,983 B1 | 2/2001 | Sun |
| 5,633,419 A | 5/1997 | Spencer et al. | | 6,203,712 B1 | 3/2001 | Bronner et al. |
| 5,639,930 A | 6/1997 | Penick | | 6,207,864 B1 | 3/2001 | Henningsen et al. |
| 5,653,956 A | 8/1997 | Zones | | 6,225,517 B1 | 5/2001 | Nascimento et al. |
| 5,656,149 A | 8/1997 | Zones et al. | | 6,248,218 B1 | 6/2001 | Linkous et al. |
| 5,661,097 A | 8/1997 | Spencer et al. | | 6,265,505 B1 | 7/2001 | McConville et al. |
| 5,663,465 A | 9/1997 | Clegg et al. | | 6,281,405 B1 | 8/2001 | Davis et al. |
| 5,663,474 A | 9/1997 | Pham et al. | | 6,320,085 B1 | 11/2001 | Arvai et al. |
| 5,674,464 A | 10/1997 | Van Velzen et al. | | 6,337,063 B1 | 1/2002 | Rouleau et al. |
| 5,675,046 A | 10/1997 | Ohno et al. | | 6,342,200 B1 | 1/2002 | Rouleau et al. |
| 5,675,052 A | 10/1997 | Menon et al. | | 6,368,490 B1 | 4/2002 | Gestermann |
| 5,679,134 A | 10/1997 | Brugerolle et al. | | 6,369,283 B1 | 4/2002 | Guram et al. |
| 5,679,879 A | 10/1997 | Mercier et al. | | 6,372,949 B1 | 4/2002 | Brown et al. |
| 5,684,213 A | 11/1997 | Nemphos et al. | | 6,376,731 B1 | 4/2002 | Evans et al. |
| 5,693,191 A | 12/1997 | Pividal et al. | | 6,380,328 B1 | 4/2002 | McConville et al. |
| 5,695,890 A | 12/1997 | Thompson et al. | | 6,380,423 B2 | 4/2002 | Banning et al. |
| 5,698,747 A | 12/1997 | Godwin et al. | | 6,380,444 B1 | 4/2002 | Bjerrum et al. |
| 5,705,712 A | 1/1998 | Frey et al. | | 6,395,945 B1 | 5/2002 | Randolph |
| 5,705,728 A | 1/1998 | Viswanathan et al. | | 6,403,840 B1 | 6/2002 | Zhou et al. |
| 5,705,729 A | 1/1998 | Huang | | 6,406,523 B1 | 6/2002 | Connor et al. |
| 5,708,246 A | 1/1998 | Camaioni et al. | | 6,423,211 B1 | 7/2002 | Randolph et al. |
| 5,720,858 A | 2/1998 | Noceti et al. | | 6,426,441 B1 | 7/2002 | Randolph et al. |
| 5,728,897 A | 3/1998 | Buysch et al. | | 6,426,442 B1 | 7/2002 | Ichikawa et al. |
| 5,728,905 A | 3/1998 | Clegg et al. | | 6,452,058 B1 | 9/2002 | Schweizer et al. |
| 5,734,073 A | 3/1998 | Chambers et al. | | 6,455,650 B1 | 9/2002 | Lipian et al. |
| 5,741,949 A | 4/1998 | Mack | | 6,462,243 B1 | 10/2002 | Zhou et al. |
| 5,744,669 A | 4/1998 | Kalnes et al. | | 6,465,696 B1 | 10/2002 | Zhou et al. |
| 5,750,801 A | 5/1998 | Buysch et al. | | 6,465,699 B1 | 10/2002 | Grosso |
| 5,770,175 A | 6/1998 | Zones | | 6,472,345 B2 | 10/2002 | Hintermann et al. |
| 5,776,871 A | 7/1998 | Cothran et al. | | 6,472,572 B1 | 10/2002 | Zhou et al. |
| 5,780,703 A | 7/1998 | Chang et al. | | 6,475,463 B1 | 11/2002 | Elomari et al. |
| 5,782,936 A | 7/1998 | Riley | | 6,475,464 B1 | 11/2002 | Rouleau et al. |
| 5,798,314 A | 8/1998 | Spencer et al. | | 6,479,705 B2 | 11/2002 | Murata et al. |
| 5,814,715 A | 9/1998 | Chen et al. | | 6,482,997 B2 | 11/2002 | Petit-Clair et al. |
| 5,817,904 A | 10/1998 | Vic et al. | | 6,486,368 B1 | 11/2002 | Zhou et al. |
| 5,821,394 A | 10/1998 | Schoebrechts et al. | | 6,491,809 B1 | 12/2002 | Briot et al. |
| 5,847,224 A | 12/1998 | Koga et al. | | 6,495,484 B1 | 12/2002 | Holtcamp |
| 5,849,978 A | 12/1998 | Benazzi et al. | | 6,509,485 B2 | 1/2003 | Mul et al. |
| 5,866,735 A | 2/1999 | Cheung et al. | | 6,511,526 B2 | 1/2003 | Jagger et al. |
| 5,882,614 A | 3/1999 | Taylor, Jr. et al. | | 6,514,319 B2 | 2/2003 | Keefer et al. |
| 5,895,831 A | 4/1999 | Brasier et al. | | 6,518,474 B1 | 2/2003 | Sanderson et al. |
| 5,898,086 A | 4/1999 | Harris | | 6,518,476 B1 | 2/2003 | Culp et al. |
| 5,905,169 A | 5/1999 | Jacobson | | 6,525,228 B2 | 2/2003 | Chauvin et al. |
| 5,906,892 A | 5/1999 | Thompson et al. | | 6,525,230 B2 | 2/2003 | Grosso |
| 5,908,963 A | 6/1999 | Voss et al. | | 6,528,693 B1 | 3/2003 | Gandy et al. |

| | | | | | | |
|---|---|---|---|---|---|---|
| 6,538,162 B2 | 3/2003 | Chang et al. | | 7,094,936 B1 | 8/2006 | Owens et al. |
| 6,540,905 B1 | 4/2003 | Elomari | | 7,098,371 B2 | 8/2006 | Mack et al. |
| 6,545,191 B1 | 4/2003 | Stauffer | | 7,105,710 B2 | 9/2006 | Boons et al. |
| 6,547,958 B1 | 4/2003 | Elomari | | 7,138,534 B2 | 11/2006 | Forlin et al. |
| 6,548,040 B1 | 4/2003 | Rouleau et al. | | 7,141,708 B2 | 11/2006 | Marsella et al. |
| 6,552,241 B1 | 4/2003 | Randolph et al. | | 7,145,045 B2 | 12/2006 | Harmsen et al. |
| 6,566,572 B2 | 5/2003 | Okamoto et al. | | 7,148,356 B2 | 12/2006 | Smith, III et al. |
| 6,572,829 B2 | 6/2003 | Linkous et al. | | 7,148,390 B2 | 12/2006 | Zhou et al. |
| 6,585,953 B2 | 7/2003 | Roberts et al. | | 7,151,199 B2 | 12/2006 | Martens et al. |
| 6,616,830 B2 | 9/2003 | Elomari | | 7,161,050 B2 | 1/2007 | Sherman et al. |
| 6,620,757 B2 | 9/2003 | McConville et al. | | 7,169,730 B2 | 1/2007 | Ma et al. |
| 6,632,971 B2 | 10/2003 | Brown et al. | | 7,176,340 B2 | 2/2007 | Van Broekhoven et al. |
| 6,635,793 B2 | 10/2003 | Mul et al. | | 7,176,342 B2 | 2/2007 | Bellussi et al. |
| 6,641,644 B2 | 11/2003 | Jagger et al. | | 7,182,871 B2 | 2/2007 | Perriello |
| 6,646,102 B2 | 11/2003 | Boriack et al. | | 7,193,093 B2 | 3/2007 | Murray et al. |
| 6,669,846 B2 | 12/2003 | Perriello | | 7,196,239 B2 | 3/2007 | Van Egmond et al. |
| 6,672,572 B2 | 1/2004 | Werlen | | 7,199,083 B2 | 4/2007 | Zevallos |
| 6,679,986 B1 | 1/2004 | Da Silva et al. | | 7,199,255 B2 | 4/2007 | Murray et al. |
| 6,680,415 B1 | 1/2004 | Gulotty, Jr. et al. | | 7,208,641 B2 | 4/2007 | Nagasaki et al. |
| 6,692,626 B2 | 2/2004 | Keefer et al. | | 7,214,750 B2 | 5/2007 | McDonald et al. |
| 6,692,723 B2 | 2/2004 | Rouleau et al. | | 7,220,391 B1 | 5/2007 | Huang et al. |
| 6,710,213 B2 | 3/2004 | Aoki et al. | | 7,226,569 B2 | 6/2007 | Elomari |
| 6,713,087 B2 | 3/2004 | Tracy et al. | | 7,226,576 B2 | 6/2007 | Elomari |
| 6,713,655 B2 | 3/2004 | Yilmaz et al. | | 7,230,150 B2 | 6/2007 | Grosso et al. |
| RE38,493 E | 4/2004 | Keefer et al. | | 7,230,151 B2 | 6/2007 | Martens et al. |
| 6,723,808 B2 | 4/2004 | Holtcamp | | 7,232,872 B2 | 6/2007 | Shaffer et al. |
| 6,727,400 B2 | 4/2004 | Messier et al. | | 7,238,846 B2 | 7/2007 | Janssen et al. |
| 6,740,146 B2 | 5/2004 | Simonds | | 7,244,795 B2 | 7/2007 | Agapiou et al. |
| 6,753,390 B2 | 6/2004 | Ehrman et al. | | 7,244,867 B2 | 7/2007 | Waycuilis |
| 6,765,120 B2 | 7/2004 | Weber et al. | | 7,250,107 B2 | 7/2007 | Benazzi et al. |
| 6,797,845 B1 | 9/2004 | Hickman et al. | | 7,250,542 B2 | 7/2007 | Smith, Jr. et al. |
| 6,797,851 B2 | 9/2004 | Martens et al. | | 7,252,920 B2 | 8/2007 | Kurokawa et al. |
| 6,821,924 B2 | 11/2004 | Gulotty, Jr. et al. | | 7,253,327 B2 | 8/2007 | Janssens et al. |
| 6,822,123 B2 | 11/2004 | Stauffer | | 7,253,328 B2 | 8/2007 | Stauffer |
| 6,822,125 B2 | 11/2004 | Lee et al. | | 7,265,193 B2 | 9/2007 | Weng et al. |
| 6,825,307 B2 | 11/2004 | Goodall | | 7,267,758 B2 | 9/2007 | Benazzi et al. |
| 6,825,383 B1 | 11/2004 | Dewkar et al. | | 7,268,263 B1 | 9/2007 | Frey et al. |
| 6,831,032 B2 | 12/2004 | Spaether | | 7,271,303 B1 | 9/2007 | Sechrist et al. |
| 6,838,576 B1 | 1/2005 | Wicki et al. | | 7,273,957 B2 | 9/2007 | Bakshi et al. |
| 6,841,063 B2 | 1/2005 | Elomari | | 7,282,603 B2 | 10/2007 | Richards |
| 6,852,896 B2 | 2/2005 | Stauffer | | 7,285,698 B2 | 10/2007 | Liu et al. |
| 6,866,950 B2 | 3/2005 | Connor et al. | | 7,304,193 B1 | 12/2007 | Frey et al. |
| 6,869,903 B2 | 3/2005 | Matsunaga | | 7,342,144 B2 | 3/2008 | Kaizik et al. |
| 6,875,339 B2 | 4/2005 | Rangarajan et al. | | 7,348,295 B2 | 3/2008 | Zones et al. |
| 6,878,853 B2 | 4/2005 | Tanaka et al. | | 7,348,464 B2 | 3/2008 | Waycuilis |
| 6,888,013 B2 | 5/2005 | Paparatto et al. | | 7,357,904 B2 | 4/2008 | Zones et al. |
| 6,900,363 B2 | 5/2005 | Harth et al. | | 7,361,794 B2 | 4/2008 | Grosso |
| 6,902,602 B2 | 6/2005 | Keefer et al. | | 7,365,102 B1 | 4/2008 | Weissman |
| 6,903,171 B2 | 6/2005 | Rhodes et al. | | 7,390,395 B2 | 6/2008 | Elomari |
| 6,909,024 B1 | 6/2005 | Jones et al. | | 7,560,607 B2 | 7/2009 | Waycuilis |
| 6,921,597 B2 | 7/2005 | Keefer et al. | | 7,674,941 B2 | 3/2010 | Waycuilis et al. |
| 6,933,417 B1 | 8/2005 | Henley et al. | | 7,713,510 B2 | 5/2010 | Harrod et al. |
| 6,946,566 B2 | 9/2005 | Yaegashi et al. | | 7,880,041 B2 | 2/2011 | Waycuilis |
| 6,953,868 B2 | 10/2005 | Boaen et al. | | 8,008,535 B2 | 8/2011 | Waycuilis |
| 6,953,870 B2 | 10/2005 | Yan et al. | | 8,173,851 B2 | 5/2012 | Waycuilis et al. |
| 6,953,873 B2 | 10/2005 | Cortright et al. | | 8,198,495 B2 | 6/2012 | Waycuilis et al. |
| 6,956,140 B2 | 10/2005 | Ehrenfeld | | 8,232,441 B2 | 7/2012 | Waycuilis |
| 6,958,306 B2 | 10/2005 | Holtcamp | | 2002/0102672 A1 | 8/2002 | Mizrahi |
| 6,984,763 B2 | 1/2006 | Schweizer et al. | | 2002/0193649 A1 | 12/2002 | O'Rear et al. |
| 7,001,872 B2 | 2/2006 | Pyecroft et al. | | 2002/0198416 A1 | 12/2002 | Zhou et al. |
| 7,002,050 B2 | 2/2006 | Santiago Fernandez et al. | | 2003/0004380 A1 | 1/2003 | Grumann |
| 7,011,811 B2 | 3/2006 | Elomari | | 2003/0065239 A1 | 4/2003 | Zhu |
| 7,019,182 B2 | 3/2006 | Grosso | | 2003/0069452 A1 | 4/2003 | Sherman et al. |
| 7,026,145 B2 | 4/2006 | Mizrahi et al. | | 2003/0078456 A1 | 4/2003 | Yilmaz et al. |
| 7,026,519 B2 | 4/2006 | Santiago Fernandez et al. | | 2003/0120121 A1 | 6/2003 | Sherman et al. |
| 7,037,358 B2 | 5/2006 | Babicki et al. | | 2003/0125589 A1 | 7/2003 | Grosso |
| 7,045,670 B2 | 5/2006 | Johnson et al. | | 2003/0166973 A1 | 9/2003 | Zhou et al. |
| 7,049,388 B2 | 5/2006 | Boriack et al. | | 2004/0006246 A1 | 1/2004 | Sherman et al. |
| 7,053,252 B2 | 5/2006 | Boussand et al. | | 2004/0062705 A1 | 4/2004 | Leduc |
| 7,057,081 B2 | 6/2006 | Allison et al. | | 2004/0152929 A1 | 8/2004 | Clarke |
| 7,060,865 B2 | 6/2006 | Ding et al. | | 2004/0158107 A1 | 8/2004 | Aoki |
| 7,064,238 B2 | 6/2006 | Waycuilis | | 2004/0158108 A1 | 8/2004 | Snoble |
| 7,064,240 B2 | 6/2006 | Ohno et al. | | 2004/0171779 A1 | 9/2004 | Matyjaszewski et al. |
| 7,067,448 B1 | 6/2006 | Weitkamp et al. | | 2004/0187684 A1 | 9/2004 | Elomari |
| 7,083,714 B2 | 8/2006 | Elomari | | 2004/0188271 A1* | 9/2004 | Ramachandraiah et al. . 205/619 |
| 7,084,308 B1 | 8/2006 | Stauffer | | 2004/0188324 A1 | 9/2004 | Elomari |
| 7,091,270 B2 | 8/2006 | Zilberman et al. | | 2004/0220433 A1 | 11/2004 | Van Der Heide |
| 7,091,387 B2 | 8/2006 | Fong et al. | | 2005/0027084 A1 | 2/2005 | Clarke |
| 7,091,391 B2 | 8/2006 | Stauffer | | 2005/0038310 A1 | 2/2005 | Lorkovic et al. |

| Pub. No. | Date | Inventor | Country | Number | Date |
|---|---|---|---|---|---|
| 2005/0042159 A1 | 2/2005 | Elomari | EP | 0510238 A1 | 10/1992 |
| 2005/0047927 A1 | 3/2005 | Lee et al. | EP | 0526908 A2 | 2/1993 |
| 2005/0148805 A1 | 7/2005 | Jones | EP | 0346612 B1 | 8/1993 |
| 2005/0171393 A1 | 8/2005 | Lorkovic | EP | 0560546 A1 | 9/1993 |
| 2005/0192468 A1 | 9/2005 | Sherman et al. | EP | 0976705 A1 | 7/1998 |
| 2005/0215837 A1 | 9/2005 | Hoffpauir | EP | 1186591 A2 | 3/2002 |
| 2005/0234276 A1 | 10/2005 | Waycuilis | EP | 1253126 A1 | 10/2002 |
| 2005/0234277 A1 | 10/2005 | Waycuilis | EP | 1312411 A2 | 5/2003 |
| 2005/0245771 A1 | 11/2005 | Fong et al. | EP | 1235769 B1 | 5/2004 |
| 2005/0245772 A1 | 11/2005 | Fong | EP | 1440939 A1 | 7/2004 |
| 2005/0245777 A1 | 11/2005 | Fong | EP | 1235772 B1 | 1/2005 |
| 2005/0267224 A1 | 12/2005 | Herling | EP | 1661620 A1 | 5/2006 |
| 2006/0025617 A1 | 2/2006 | Begley | EP | 1760057 A1 | 3/2007 |
| 2006/0100469 A1 | 5/2006 | Waycuilis | EP | 1689728 B1 | 4/2007 |
| 2006/0135823 A1 | 6/2006 | Jun | EP | 1808227 A1 | 7/2007 |
| 2006/0138025 A1 | 6/2006 | Zones | EP | 1837320 A1 | 9/2007 |
| 2006/0138026 A1 | 6/2006 | Chen | GB | 5125 | 0/1912 |
| 2006/0149116 A1 | 7/2006 | Slaugh | GB | 156122 | 3/1922 |
| 2006/0229228 A1 | 10/2006 | Komon et al. | GB | 294100 | 6/1929 |
| 2006/0229475 A1 | 10/2006 | Weiss et al. | GB | 363009 | 12/1931 |
| 2006/0270863 A1 | 11/2006 | Reiling | GB | 402928 | 12/1933 |
| 2006/0288690 A1 | 12/2006 | Elomari | GB | 474922 A | 11/1937 |
| 2007/0004955 A1 | 1/2007 | Kay | GB | 536491 | 5/1941 |
| 2007/0078285 A1 | 4/2007 | Dagle | GB | 553950 | 6/1943 |
| 2007/0100189 A1 | 5/2007 | Stauffer | GB | 586483 | 3/1947 |
| 2007/0129584 A1 | 6/2007 | Basset | GB | 775590 | 5/1957 |
| 2007/0142680 A1 | 6/2007 | Ayoub | GB | 793214 | 4/1958 |
| 2007/0148067 A1 | 6/2007 | Zones | GB | 796048 | 6/1958 |
| 2007/0148086 A1 | 6/2007 | Zones | GB | 796085 | 6/1958 |
| 2007/0149778 A1 | 6/2007 | Zones | GB | 883256 | 11/1961 |
| 2007/0149789 A1 | 6/2007 | Zones | GB | 883256 A | 11/1961 |
| 2007/0149819 A1 | 6/2007 | Zones | GB | 930341 A | 7/1963 |
| 2007/0149824 A1 | 6/2007 | Zones | GB | 950975 | 3/1964 |
| 2007/0149837 A1 | 6/2007 | Zones | GB | 950976 | 3/1964 |
| 2007/0197801 A1 | 8/2007 | Bolk | GB | 991303 | 5/1965 |
| 2007/0197847 A1 | 8/2007 | Liu | GB | 995960 | 6/1965 |
| 2007/0213545 A1 | 9/2007 | Bolk | GB | 1015033 | 12/1965 |
| 2007/0238905 A1 | 10/2007 | Arredondo | GB | 1104294 | 2/1968 |
| 2007/0238909 A1* | 10/2007 | Gadewar et al. ........... 585/16 | GB | 1133752 | 11/1968 |
| 2007/0276168 A1 | 11/2007 | Garel | GB | 1172002 | 11/1969 |
| 2007/0284284 A1 | 12/2007 | Zones | GB | 1212240 | 11/1970 |
| 2008/0022717 A1 | 1/2008 | Yoshida et al. | GB | 1233299 | 5/1971 |
| 2008/0152555 A1 | 6/2008 | Wang et al. | GB | 1253618 | 11/1971 |
| 2008/0171898 A1 | 7/2008 | Waycuilis | GB | 1263806 A | 2/1972 |
| 2008/0183022 A1 | 7/2008 | Waycuilis | GB | 1446803 | 8/1976 |
| 2008/0188697 A1 | 8/2008 | Lorkovic | GB | 1542112 | 3/1979 |
| 2008/0200740 A1 | 8/2008 | Waycuilis | GB | 2095243 A | 9/1982 |
| 2008/0275284 A1 | 11/2008 | Waycuilis | GB | 2095245 A | 9/1982 |
| 2008/0314758 A1* | 12/2008 | Grosso et al. ........... 205/431 | GB | 2095249 A | 9/1982 |
| 2009/0005620 A1 | 1/2009 | Waycuilis et al. | GB | 2116546 A | 9/1982 |
| 2009/0163749 A1 | 6/2009 | Li et al. | GB | 2120249 A | 11/1983 |
| 2009/0247796 A1 | 10/2009 | Waycuilis et al. | GB | 2185754 A | 7/1987 |
| 2009/0270655 A1 | 10/2009 | Fong et al. | GB | 2191214 A | 12/1987 |
| 2009/0306443 A1 | 12/2009 | Stark et al. | SU | 694483 A1 | 10/1979 |
| 2009/0312586 A1 | 12/2009 | Waycuilis et al. | WO | 83/00859 | 3/1983 |
| 2009/0326292 A1 | 12/2009 | Waycuilis | WO | 85/04863 | 11/1985 |
| 2010/0030005 A1 | 2/2010 | Sauer et al. | WO | 85/04867 | 11/1985 |
| 2010/0087686 A1 | 4/2010 | Fong et al. | WO | 90/08120 | 7/1990 |
| 2010/0096588 A1 | 4/2010 | Gadewar et al. | WO | 90/08752 | 8/1990 |
| 2010/0099930 A1 | 4/2010 | Stoimenov et al. | WO | 91/18856 | 12/1991 |
| 2010/0105972 A1 | 4/2010 | Lorkovic | WO | 92/03401 | 3/1992 |
| 2010/0234637 A1 | 9/2010 | Fong et al. | WO | 92/12946 | 8/1992 |
| 2011/0015458 A1 | 1/2011 | Waycuilis et al. | WO | 93/16798 | 9/1993 |
| 2011/0071326 A1 | 3/2011 | Waycuilis | WO | 96/22263 | 7/1996 |
| 2011/0218372 A1 | 9/2011 | Waycuilis et al. | WO | 97/44302 | 11/1997 |
| 2011/0218374 A1 | 9/2011 | Waycuilis | WO | 98/12165 | 3/1998 |
| 2012/0141356 A1 | 6/2012 | Brickey et al. | WO | 99/07443 | 2/1999 |
| | | | WO | 00/07718 A1 | 2/2000 |
| FOREIGN PATENT DOCUMENTS | | | WO | 00/09261 A1 | 2/2000 |
| CA | 1101441 | 5/1981 | WO | 01/14300 A1 | 3/2001 |
| CA | 1202610 | 4/1986 | WO | 01/38275 A1 | 5/2001 |
| CA | 2542857 | 5/2005 | WO | 01/44149 A1 | 6/2001 |
| CA | 2236126 | 8/2006 | WO | 02/094749 A1 | 11/2002 |
| CA | 2203115 | 9/2006 | WO | 02/094750 A1 | 11/2002 |
| CA | 2510093 | 12/2006 | WO | 02/094751 A2 | 11/2002 |
| EP | 0164798 A1 | 12/1985 | WO | 02/094752 A1 | 11/2002 |
| EP | 0418971 A1 | 3/1991 | WO | 03/000635 A1 | 1/2003 |
| EP | 0418974 A1 | 3/1991 | WO | 03/002251 A2 | 1/2003 |
| EP | 0418975 A1 | 3/1991 | WO | 03/018524 A1 | 3/2003 |

| | | |
|---|---|---|
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006-067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/076942 A1 | 7/2006 |
| WO | 2006/083427 A2 | 8/2006 |
| WO | 2006-100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |
| WO | 2008/157047 A1 | 12/2008 |
| WO | 2009/152403 A1 | 12/2009 |
| WO | 2009/152405 A1 | 12/2009 |
| WO | 2009/152408 A1 | 12/2009 |
| WO | 2010/009376 A1 | 1/2010 |
| WO | 2011/008573 A1 | 1/2011 |
| WO | 2011/109244 A2 | 9/2011 |
| WO | 2011/159490 A1 | 12/2011 |

OTHER PUBLICATIONS

Abstract of GB 998681 (A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jun. 3, 1980, Inventor: Shigeo et al, http://www19.ipdl.inpit.go.jp/PA1/result . . . .

Hannus; "Adsorption and Transformation of Halogenated Hydrocarbons Over Zeolites", Applied Catalysis A: General 189; 1999; XP-002634422; pp. 263-276.

Howe; "Zeolite Catalysts for Dehalogenation Processes"; Applied Catalysis A: General 271; 2004; XP-002634421; pp. 3-11.

Li et al.; "Pyrolysis of Halon 1301 Over Zeolite Catalysts"; Microporous and Mesoporous Materials 35-36; 2000; XP-002634423; pp. 219-226.

U.S. Office Communication from U.S. Appl. No. 12/112,926 dated Jan. 7, 2011.

U.S. Office Communication from U.S. Appl. No. 12/502,024 dated May 31, 2011.

U.S. Office Communication from U.S. Appl. No. 12/715,526 dated Feb. 17, 2011.

U.S. Office Communication from U.S. Appl. No. 12/715,526 dated May 24, 2011.

U.S. Office Communication from U.S. Appl. No. 12/139,135 dated Apr. 14, 2011.

Liu et al.; "Higher Hydrocarbons from Methane Condensation Mediated by HBr"; Journal of Molecular Catalysis A: Chemical 273; Elsevier B.V. 2007; pp. 14-20.

U.S. Office Action from U.S. Appl. No. 11/778,479 dated Feb. 22, 2010.

U.S. Office Action from U.S. Appl. No. 12/123,924 dated Mar. 19, 2010.

Olah et al.; Hydrocarbons Through Methane Derivatives; Hydrocarbon Chemistry 2nd Edition; 2003; John Wiley & Sons, Inc.; pp. 123, 149, and 153.

Rakoff et al.; Quimica Organica Fundamental; The Macmillan Company; 1966; pp. 58-63 and 76-77.

U.S. Office Action from U.S. Appl. No. 12/112,926 dated Jan. 16, 2009.

U.S. Office Action from U.S. Appl. No. 12/112,926 dated Sep. 14, 2009.

U.S. Office Action from U.S. Appl. No. 12/112,926 dated Jan. 7, 2010.

U.S. Appl. No. 60/487,364, filed Jul. 15, 2003, Lorkovic et al.

U.S. Appl. No. 60/559,844, filed Apr. 6, 2004, Sherman et al.

Abstract of EP0021497 (A1), Synthesis of polyoxyalkylene glycol monoalkyl ethers, Publication date: Jan. 7, 1981, Inventor: Gibson, esp@cenet database—worldwide.

U.S. Office Action from U.S. Appl. No. 10/365,346 dated Jun. 12, 2006.

U.S. Office Action from U.S. Appl. No. 10/893,418 dated Jun. 14, 2007.

U.S. Office Action from U.S. Appl. No. 10/893,418 dated Jan. 2, 2008.

U.S. Office Action from U.S. Appl. No. 11/091,130 dated Oct. 3, 2007.

Benizri et al., Study of the Liquid-Vapor Equilibrium in the Bromine-Hydrobromic Acid-Water System, Hydrogen Energy Vector, 1980, pp. 101-116.

Bradshaw et al., Production of Hydrobromic Acid from Bromine and Methane for Hydrogen Production, Proceedings of the 2001 DOE Hydrogen Program Review, NREL/CP-570-30535, 2001.

Motupally et al., Recycling Chlorine from Hydrogen Chloride, The Electrochemical Society Interface, Fall 2008, pp. 32-36.

Wauters et al., Electrolytic Membrane Recovery of Bromine from Waste Hydrogen Bromide Streams, AIChE Journal, Oct. 1998, vol. 44, No. 10, pp. 2144-2148.

Kirk-Othmer Encyclopedia of Chemical Technology, 4th Edition, vol. 1, A Wiley-Interscience Publication, John Wiley & Sons, 1991, pp. 946-997.

Adachi et al., Synthesis of Sialyl Lewis X Ganglioside Analogs Containing a Variable Length Spacer Between the Sugar and Lipophilic Moieties, J. Carbohydrate Chemistry, vol. 17, No. 4-5, 1998, pp. 595-607; XP009081720.

Bakker et al., An Exploratory Study of the Addition Reactions of Ethyleneglycol, 2-Chloroethanol and 1,3-Dichloro-2-Propanol to 1-Dodecene, J. Am. Oil Chem. Soc., vol. 44, No. 9, 1967, pp. 517-521; XP009081570.

Bouzide et al., Highly Selective Silver (I) Oxide Mediated Monoprotection of Symmetrical Diols, Tetrahedron Letters, Elsevier, vol. 38, No. 34, 1997, pp. 5945-5948; XP004094157.

Gibson et al., Phase-Transfer Synthesis of Monoalkyl Ethers of Oligoethylene Glycols, J. Org. Chem., vol. 45, No. 6, 1980, pp. 1095-1098; XP002427776.

Loiseau et al., Multigram Synthesis of Well-Defined Extended Bifunctional Polyethylene Glycol (PEG) Chains, J. Org. Chem., vol. 69, No. 3, 2004, pp. 639-647; XP002345040.

Mihai et al., Application of Bronsted-Type LFER in the Study of the Phospholipase C Mechanism, J. Am. Chem. Soc., vol. 125, No. 11, 2003, pp. 3236-3242; XP002427777.

Nishikawa et al., Ultrasonic Relaxations in Aqueous Solutions of Alcohols and the Balance between Hydrophobicity and Hydrophilicity of the Solutes, J. Phys. Chem., vol. 97, No. 14, 1993, pp. 3539-3544; XP002427775.

Prelog et al., Chirale 2,2'-Polyoxaalkano-9,9'-Spirobifluorene, Helvetica Chimica Acta, vol. 62, No. 7, 1979, pp. 2285-2302; XP002030901.

Shimizu et al., Gas-Phase Electrolysis of Hydrobromic Acid Using PTFE-Bonded Carbon Electrode, Int. J. Hydrogen Energy, vol. 13, No. 6, pp. 345-349, 1988.

Velzen et al., HBr Electrolysis in the Ispra Mark 13A Flue Gas Desulphurization Process: Electrolysis in a DEM Cell, J. of Applied Electrochemistry, vol. 20, pp. 60-68, 1990.

Whitesides et al., Nuclear Magnetic Resonance Spectroscopy. The Effect of Structure on Magnetic Nonequivalence Due to Molecular Asymmetry, J. Am. Chem. Soc., vol. 86, No. 13, 1964, pp. 2628-2634; XP002427774.

Combined International Search Report and Written Opinion Dated Apr. 17, 2007 for PCT/US2006/13394, in the name of GRT, Inc.

U.S. Appl. No. 60/765,115, filed Feb. 6, 2006, Gadewar et al.

JLM Technology Ltd.; "The Miller GLS Technology for Conversion of Light Hydrocarbons to Alcohols"; New Science for the Benefit of Humanity; May 31, 2000; pp. 1-10.

Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.

Taylor, Charles E.; "Conversion of Substituted Methanes Over ZSM-Catalysts"; 2000; pp. 3633-3638; Studies in Surface Science and Catalysis 130; Elsevier Science B.V.

ZSM-5 Catalyst; http://chemelab.ucsd.edu/methanol/memos/ZSM-5.html; Nov. 6, 2003; p. 1.

Final Report; "Abstract"; http://chemelab.ucsd.edu/methanol/memos/final.html; May 9, 2004; pp. 1-7.

Driscoll, Daniel J.; "Direct Methane Conversion"; Federal Energy Technology Center, U.S. Department of Energy; M970779; pp. 1-10.

Olah et al.; "Selective Monohalogenation of Methane over Supported Acid or Platinum Metal Catalysts and Hydrolysis of Methyl Halides . . . "; J. American Chemical Society 1985, vol. 107; 0002-7863/85/1507-7097$01.50/0; pp. 7097-7105.

Murray et al.; "Conversion of Methyl Halides to Hydrocarbons on Basic Zeolites: A Discovery by in Situ NMR"; J. American Chemical Society 1993, vol. 115; pp. 4732-4741.

Lorkovic et al.; "A Novel Integrated Process for the Functionalization of Methane and Ethane: Bromine as Mediator", Catalysis Today 98; 2004; pp. 317-322.

Lorkovic et al.; "C1 Oxidative Coupling via Bromine Activation and Tandem Catalytic Condensation over CaO/ Zeolite Composites II . . . "; Catalysis Today 98; 2004; pp. 589-594.

Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.

Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.

Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.

Zhou, Xiao-Ping et al.; "An Integrated Process for Partial Oxidation of Alkanes"; Chem. Commun. 2003; The Royal Society of Chemistry 2003; pp. 2294-2295.

Sun, Shouli et al.; "A General Integrated Process for Synthesizing Olefin Oxides"; Chem. Commun. 2004; The Royal Society of Chemistry 2004; pp. 2100-2101.

Lorkovic, Ivan M. et al.; "C1 Oxidative Coupling via Bromine Activation and Tandem Catalytic Condensation and Neutralization over CaO/Zeolite Composites II . . . "; Catalysis Today 98; 2004; pp. 589-594.

Yilmaz, Aysen et al.; "Bromine Mediated Partial Oxidation of Ethane over Nanostructured Zirconia Supported Metal Oxide/Bromide"; Microporous and Mesporous Materials, 79; 2005; pp. 205-214.

Taylor, Charles E.; "PETC's On-Site Natural Gas Conversion Efforts"; Preprints of the Fuel Division, 208th National Meeting of the American Chemical Society, 39 (4); 1994; pp. 1228-1232.

Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.

Olah, George A. et al.; "Hydrocarbons Through Methane Derivatives"; Hydrocarbon Chemistry; 1995; pp. 89-90; John Wiley & Sons, Inc.

Akhrem, Irene S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.

Smirnov, Vladimir V. et al.; "Selective Bromination of Alkanes and Arylalkanes with CBr4"; Mendeleev Commun. 2000; pp. 175-176.

Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.

Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.

Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.

Mochida, Isco et al.; "The Catalytic Dehydrohalogenation of Haloethanes on Solid Acids and Bases"; Bulletin of the Chemical Society of Japan, vol. 44; 1971; pp. 3305-3310.

Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.

Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.

Mishakov, Ilya V. et al.; "Nanocrystalline MgO as a Dehydrohalogenation Catalyst"; Journal of Catalysis 206; 2002; pp. 40-48; Elsevier Science, USA.

Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.

Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.

http://webbook.nist.gov/; "Welcome to the NIST Chemistry WebBook"; 2005; U.S. Secretary of Commerce on Behalf of the United States of America.

Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.

Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.

Thomas, John Meurig et al.; "Catalytically Active Centres in Porous Oxides: Design and Performance of Highly Selective New Catalysts"; Chem. Commun.; 2001; pp. 675-687.

Lorkovic, Ivan et al.; "C1 Coupling via Bromine Activation and Tandem Catalytic Condensation and Neutralization over CaO/Zeolite Composites"; Chem. Commun., 2004; pp. 566-567.

Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.

Weissermel, Klaus et al.; "Industrial Organic Chemistry"; 3rd Edition 1997. pp. 160-162, and 208.

Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.

Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.

Abstract of EP 1474371, Integrated process for synthesizing alcohols, ethers, and olefins from alkanes, Publication date: Nov. 10, 2004, Inventor: Zhou et al., esp@cenet database—worldwide.

Abstract of EP 1404636, Integrated process for synthesizing alcohols and ethers from alkanes, Publication date: Apr. 7, 2004, Inventor: Zhou et al., esp@cenet database—worldwide.

Abstract of CA 2447761 A1, Oxidative halogenation of C1 hydrocarbons to halogenated C1 hydrocarbons and integrated processes related thereto, Publication date: Nov. 28, 2002, Inventor: Hickman et al.

Abstract of CA 2471295 A1, Integrated process for synthesizing alcohols, ethers; and olefins from alkanes, Publication date: Jul. 31 2003, Inventor: Sherman et al.

Abstract of EP 1435349 A2, Integrated process for synthesizing alcohols and ethers from alkanes, Publication date: Jul. 7, 2004, Inventor: Zhou et al.

Abstract of JP 2004-529189 (best available copy).

Abstract of BE812868, Aromatic hydrocarbons prodn. from chlorinated hydrocarbons, Publication date: Sep. 27, 1974, esp@cenet database—worldwide.

Abstract of BE814900, Volatile aramatic cpds. prodn., Publication date: Sep. 2, 1974, esp@cenet database—worldwide.

Abstract of CN1199039, Pentanol and its production process, Publication date: Nov. 18, 1998, Inventor: Kailun, esp@cenet database—worldwide.

Abstract of CN1210847, Process for producing low carbon alcohol by directly hydrating low carbon olefines, Publication date: Mar. 17, 1999, Inventor: Zhenguo et al., esp@cenet database—worldwide.

Abstract of CN1321728, Method for preparing aromatic hydrocarbon and hydrogen gas by using low-pressure gas, Publication date: Nov. 14, 2001, Inventor: Jie et al., esp@cenet database—worldwide.

Abstract of CN1451721, Process for non-catalytic combustion deoxidizing coal mine gas for producing methanol, Publication date: Oct. 29, 2003, Inventor: Pengwan et al., esp@cenet database—worldwide.

Abstract of CN1623969, Method for preparing 1, 4-benzene dimethanol, Publication date: Jun. 8, 2005, Inventor: Jiarong et al., esp@cenet database—worldwide.

Abstract of CN1657592, Method for converting oil to multiple energy fuel product, Publication date: Aug. 24, 2005, Inventor: Li, esp@cenet database—worldwide.

Abstract of CN1687316, Method for producing biologic diesel oil from rosin, Publication date: Oct. 26, 2005, Inventor: Jianchun et al., esp@cenet database—worldwide.

Abstract of CN1696248, Method for synthesizing biologic diesel oil based on ion liquid, Publication date: Nov. 16, 2005, Inventor: Sun, esp@cenet database—worldwide.

Abstract of CN1699516, Process for preparing bio-diesel-oil by using microalgae fat, Publication date: Nov. 23, 2005, Inventor: Miao, esp@cenet database—worldwide.

Abstract of CN1704392, Process for producing alkylbenzene, Publication date: Dec. 7, 2005, Inventor: Gao, esp@cenet database—worldwide.

Abstract of CN1724612, Biological diesel oil catalyst and method of synthesizing biological diesel oil using sai catalyst, Publication date: Jan. 26, 2006, Inventor: Gu, esp@cenet database—worldwide.

Abstract of CN1986737, Process of producing biodiesel oil with catering waste oil, Publication date: Jun. 27, 2007, Inventor: Chen, esp@cenet database—worldwide.

Abstract of CN100999680, Esterification reaction tech. of preparing biodiesel by waste oil, Publication date: Jul. 18, 2007, Inventor: Weiming, esp@cenet database—worldwide.

Abstract of CN101016229, Refining method for bromomeoamyl alcohol, Publication date: Aug. 15, 2007, Inventor: Tian, esp@cenet database—worldwide.

Abstract of DE3209964, Process for the preparation of chlorinated hydrocarbons, Publication date: Nov. 11, 1982, Inventor: Pyke et al., esp@cenet database—worldwide.

Abstract of DE3210196, Process for the preparation of a monochlorinated olefin, Publication date: Jan. 5, 1983, Inventor: Pyke et al., esp@cenet database—worldwide.

Abstract of DE3226028, Process for the preparation of monochlorinated olefin, Publication date: Feb. 3, 1983, Inventor: Pyke et al., esp@cenet database—worldwide.

Abstract of DE3334225, Process for the preparation of 1, 2-dichloroethane, Publication date: Aug. 4, 1985, Inventor: Hebgen et al., esp@cenet database—worldwide.

Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.

Abstract of DE4434823, Continuous prodn. Of hydroxy-benzyl alkyl ether, Publication date: Apr. 4, 1996, Inventor: Stein et al., esp@cenet database—worldwide.

Abstract of FR2692259, Aromatisation of 2-4C hydrocarbons—using a fixed-mobile-catalytic bed process, Publication date: Dec. 17, 1993, Inventor: Alario et al., esp@cenet database—worldwide.

Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.

Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.

Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2- dichloroethane from reactor, Publication date: Oct. 6, 2006, Inventor: Balthasart et al., esp@cenet database—worldwide.

Abstract of IT1255246, Process for the preparation of dinitrodiphenylmethanes, Publication date: Oct. 20, 1995, Applicant: Enichem Spa et al., esp@cenet database—worldwide.
Abstract of IT1255358, Process for the synthesis of 1, 4-butanediol, Publication date: Oct. 31, 1995, Inventor: Marco, esp@cenet database—worldwide.
Abstract of JP2142740, Production of fluoroalcohol, Publication date: May 31, 1990, Inventor: Tsutomu et al., esp@cenet database—worldwide.
Abstract of JP2144150, Chemical process and catalyst used therefore, Publication date: Jun. 1, 1990, Inventor: Deidamusu et al., esp@cenet database—worldwide.
Abstract of JP4305542, Production of halogenated hydrocarbon compounds, Publication date: Oct. 28, 1992, Inventor: Shinsuke et al., esp@cenet database—worldwide.
Abstract of JP6172225, Method for fluorinating halogenated hydrocarbon, Publication date: Jun. 21, 1994, Inventor: Takashi et al., esp@cenet database—worldwide.
Abstract of JP6206834, Production of tetrachloroethanes, Publication date: Jul. 26, 1994, Inventor: Toshiro et al., esp@cenet database—worldwide.
Abstract of JP8266888, Method for decomposing aromatic halogen compound, Publication date: Oct. 15, 1996, Inventor: Yuuji et al., esp@cenet database—worldwide.
Abstract of JP2001031605, Production of 3-hydroxy-1-cycloalkene, Publication date: Feb. 6, 2001, Inventor: Hideo et al, esp@cenet database—worldwide.
Abstract of JP2004075683, Method for producing optically active halogenohydroxypropyl compound and glycidyl compound, Publication date: Mar. 11, 2004, Inventor: Keisuke et al., esp@cenet database—worldwide.
Abstract of JP2004189655, Method for fluorinating with microwave, Publication date: Jul. 8, 2004, Inventor: Masaharu et al., esp@cenet database—worldwide.
Abstract of JP2005075798, Method for Producing adamantyl ester compound, Publication date: Mar. 24, 2005, Inventor: Norihiro et al., esp@cenet database—worldwide.
Abstract of JP2005082563, Method for producing 1, 3-adamantanediol, Publication date: Mar. 31, 2005, Inventor: Norihiro et al., esp@cenet database—worldwide.
Abstract of JP2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP2005254092, Method of manufacturing alkynes, Publication date: Sep. 22, 2005, Inventor: Shirakawa Eiji, esp@cenet database—worldwide.
Abstract of JP2006151892, Preparation method of alcohol derivative, Publication date: Jun. 15, 2006, Inventor: Baba Akio et al., esp@cenet database—worldwide.
Abstract of JP2006152263, Organic-inorganic hybrid-type mesoporous material, method for producing the same, and solid catalyst, Publication date: Jun. 15, 2006, Inventor: Junko et al., esp@cenet database—worldwide.
Abstract of JP2006193473, Aryl polyadamantane derivative having carboxy or acid anhydride group and method for producing the same, Publication date: Jul. 27, 2006, Inventor: Yasuto et al., esp@cenet database—worldwide.
Abstract of JP2006231318, Phosphorus containing macromolecule immobilizing palladium catalyst and method for using the same, Publication date: Sep. 7, 2006, Inventor: Osamu et al., esp@cenet database—worldwide.
Abstract of JP2006263567, Optical resolution method of optical isomer and optical resolution device, Publication date: Oct. 5, 2006, Inventor: Yoshikazu et al., esp@cenet database—worldwide.
Abstract of JP2006265157, Method for catalytically activating silicated nucleating agent using phosphazene base, Publication date: Oct. 5, 2006, Inventor: Yoshinori et al., esp@cenet database—worldwide.
Abstract of JP2006306758, Method for producing biaryl compound, Publication date: Nov. 9, 2006, Inventor: Yuji et al., esp@cenet database—worldwide.
Abstract of JP2007001942, Production method of para-xylene, Publication date: Jan. 11, 2007, Inventor: Kazuyoshi, esp@cenet database—worldwide.
Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
U.S. Office Action from U.S. Appl. No. 12/112,926 dated Jul. 22, 2010.
U.S. Office Action from U.S. Appl. No. 12/123,924 dated Aug. 30, 2010.
U.S. Office Action from U.S. Appl. No. 12/502,024 dated Oct. 26, 2010.
U.S. Office Action from U.S. Appl. No. 12/139,135 dated Nov. 24, 2010.
Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP2007061594, Method for decomposing organohalogen compound and mobile decomposition system, Publication date: Mar. 15, 2007, Inventor: Koichi et al., esp@cenet database—worldwide.
Abstract of JP2007099729, Method for producing alpha-methylstyrene or cumene, Publication date: Apr. 19, 2007, Inventor: Toshio, esp@cenet database—worldwide.
Abstract of RO119778, Process for preparing perchloroethylene, Publication date: Mar. 30, 2005, Inventor: Horia et al., esp@cenet database—worldwide.
Abstract of WO0105737, Method for preparing a carboxylic acid, Publication date: Jan. 25, 2001, Inventor: Pascal et al., esp@cenet database—worldwide.
Abstract of WO0105738, Method for preparing a carboxylic acid, Publication date: Jan. 25, 2001, Inventor: Pascal et al., esp@cenet database—worldwide.
Abstract of WO2004092099, Method for producing cyclic enols, Publication date: Oct. 28, 2004, Inventor: Marko et al., esp@cenet database—worldwide.
Abstract of WO2006063852, Electroluminescent polymers and use thereof, Publication date: Jun. 22, 2006, Inventor: Arne et al., esp@cenet database—worldwide.
Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO2007028761, Method for chlorinating alcohols, Publication date: Mar. 15, 2007, Inventor: Rohde et al., esp@cenet database—worldwide.
Abstract of WO2007128842, Catalytic transalkylation of dialkyl benzenes, Publication date: Nov. 15, 2007, Inventor: Goncalvesalmeida et al., esp@cenet database—worldwide.
Abstract of WO2007137566, Method for catalytic conversion of organic oxygenated compounds from biomaterials, Publication date: Dec. 6, 2007, Inventor: Reschetilowski, esp@cenet database—worldwide.
Abstract of WO9721656, Method for making fluoroalkanols, Publication date: Jun. 19, 1997, Inventor: Gillet, esp@cenet database—worldwide.
Abstract of WO9950213, Method for producing dialkyl ethers, Publication date: Oct. 7, 1999, Inventor: Falkowski Juergen et al., esp@cenet database—worldwide.
Abstract of WO2006076942, Method for the production of synthetic fuels from oxygenates, Publication date: Jul. 27, 2006, Inventor: Rothaemel et al., esp@cenet database—worldwide.
Abstract of EP0039471, Process for the preparation of 2-chloro-1,1,1,2,3,3,3-heptafluoropropane, Publication date: Nov. 11, 1981, Inventor: Von Halasz, esp@cenet database—worldwide.
Abstract of EP0101337, Process for the production of methylene chloride, Publication date: Feb. 22, 1984, Inventor: Olah et al., esp@cenet database—worldwide.
Abstract of EP0407989, Method for the production of 1,1,1-trifluoro-2,2-dichloroethane by photochlorination, Publication date: Jan. 16, 1991, Inventor: Cremer et al., esp@cenet database—worldwide.

Abstract of EP0442258, Process for the preparation of a polyunsaturated olefin, Publication date: Aug. 21, 1991, Inventor: Gaudin et al., esp@cenet database—worldwide.

Abstract of EP0465294, Process for the preparation of unsaturated bromides, Publication date: Jan. 8, 1992, Inventor: Decaudin et al., esp@cenet database—worldwide.

Abstract of EP0549387, Synthesis of n-perfluorooctylbromide, Publication date: Jun. 30, 1993, Inventor: Driven et al., esp@cenet database—worldwide.

Abstract of EP0850906, Process and apparatus for the etherification of olefinic hydrocarbon feedstocks, Publication date: Jul. 1, 1998, Inventor: Masson, esp@cenet database—worldwide.

Abstract of EP0858987, Process for the conversion of lighter alkanes to higher hydrocarbons, Publication date: Aug. 19, 1998, Inventor: Amariglio et al., esp@cenet database—worldwide.

Abstract of EP1404636, Integrated process for synthesizing alcohols and ethers from alkanes, Publication date: Apr. 7, 2004, Inventor: Zhou et al., esp@cenet database—worldwide.

Abstract of EP0235110, Process for the stabilization of silicalite catalysts, Publication date: Sep. 2, 1987, Inventor: Debras et al., esp@cenet database—worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 2, 2006.

U.S. Office Action from U.S. Appl. No. 10/826,885 dated Jan. 24, 2007.

U.S. Office Action from U.S. Appl. No. 11/101,886 dated Jan. 24, 2007.

U.S. Office Action from U.S. Appl. No. 11/254,438 dated Jan. 24, 2007.

U.S. Office Action from U.S. Appl. No. 11/254,438 dated Nov. 1, 2007.

Chretien; "Process for the Adjustment of the HHV in the LNG Plants"; 23rd World Gas Conference; Amsterdam 2006; Jun. 5-Sep. 2006; pp. 1-14.

U.S. Office Communication from U.S. Appl. No. 12/139,135 dated Oct. 14, 2011.

U.S. Office Communication from U.S. Appl. No. 12/477,319 dated Jul. 22, 2011.

U.S. Office Communication from U.S. Appl. No. 12/502,024 dated Sep. 16, 2011.

Yang et al., "Maximising the Value of Surplus Ethane and Cost-Effective Design to Handle Rich LNG"; publ. date Jun. 1, 2007; pp. 1-13.

U.S. Office Communication from U.S. Appl. No. 12/715,526 dated Jan. 4, 2012.

U.S. Office Communication from U.S. Appl. No. 13/157,584 dated May 11, 2012.

Jacobson, C.A., "Encyclopedia of Chemical Reactions", vol. 1, 1946, pp. 722.

U.S. Office Communication from U.S. Appl. No. 12/792,335 dated Aug. 17, 2012.

U.S. Office Communication from U.S. Appl. No. 12/957,036 dated Aug. 16, 2012.

U.S. Office Communication from U.S. Appl. No. 13/157,584 dated Aug. 29, 2012.

Henshuiinkai, Kagaku Daijiten, Kyoritsu Publisher Japan, Oct. 15, 1963, pp. 652-654 (no English translation).

* cited by examiner

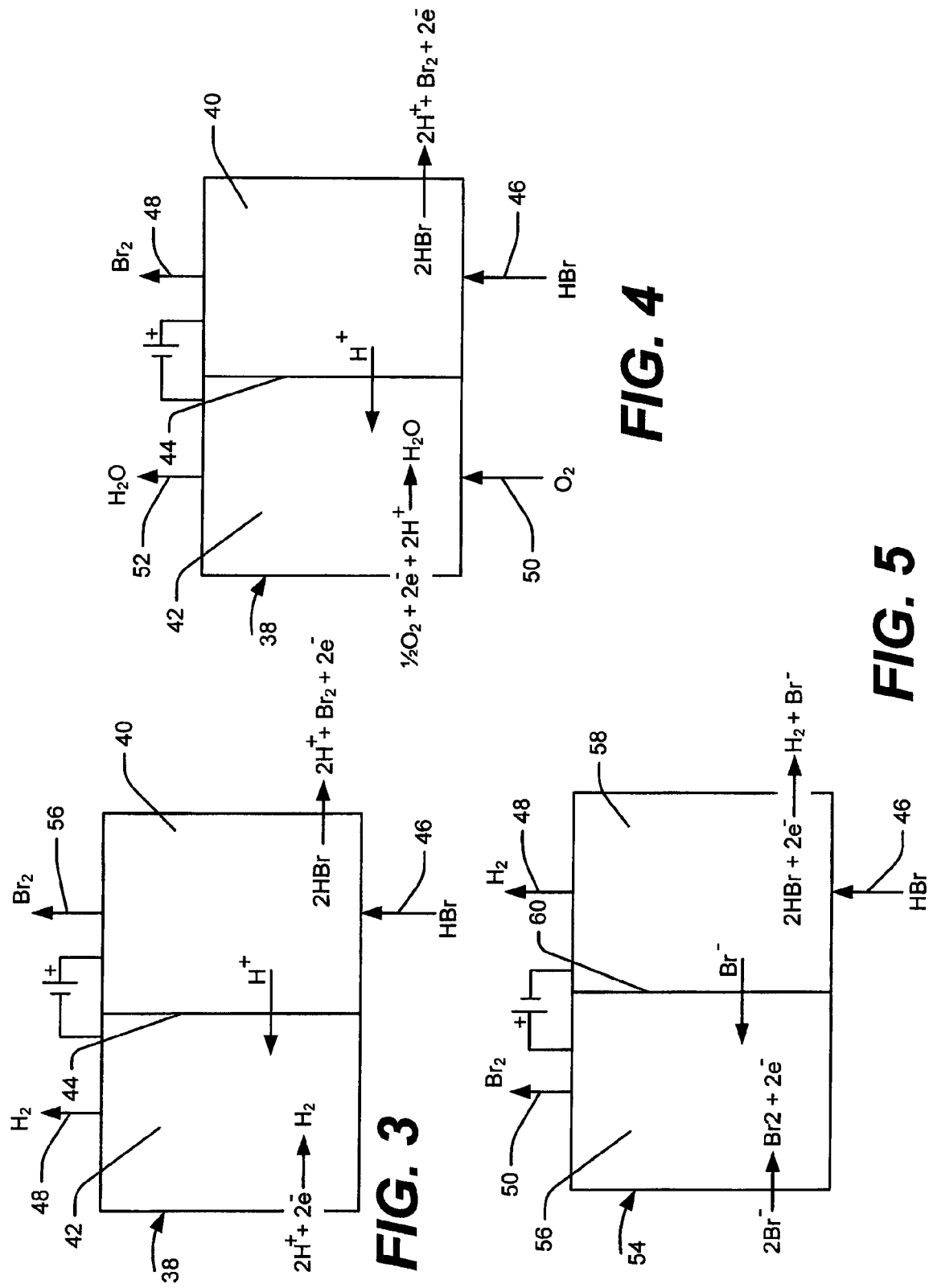

BROMINE-BASED METHOD AND SYSTEM FOR CONVERTING GASEOUS ALKANES TO LIQUID HYDROCARBONS USING ELECTROLYSIS FOR BROMINE RECOVERY

CROSS REFERENCE TO RELATED APPLICATIONS

This application is based on and claims priority to U.S. Provisional Patent Application No. 61/061,475, filed Jun. 13, 2008, the entire contents of which are incorporated by reference herein.

BACKGROUND

The present invention relates to conversion of gaseous alkanes to liquid hydrocarbons and, more particularly, in one or more embodiments, to a method and system that includes bromination of alkanes followed by conversion of the brominated alkanes to hydrocarbons wherein bromine recovery includes electrolysis.

Natural gas which primarily comprises methane and other light alkanes has been discovered in large quantities throughout the world. Many of the locales in which natural gas has been discovered are far from populated regions which have significant gas pipeline infrastructure or market demand for natural gas. Due to the low density of natural gas, its transportation in gaseous form by pipeline or as compressed gas in vessels is expensive. Accordingly, practical and economic limits exist to the distance over which natural gas may be transported in gaseous form. Cryogenic liquefaction of natural gas (LNG) is often used to more economically transport natural gas over large distances. However, this LNG process may be expensive and there are limited regasification facilities in only a few countries that are equipped to import LNG.

A number of techniques may be used to convert alkanes found in natural gas to liquids that may be more easily transported and, thus, generate additional value from natural gas. One technique for this conversion is a bromine-based process that may include bromination of alkanes to form brominated alkanes, and conversion of the brominated alkanes to hydrocarbons over an appropriate catalyst. An undesirable by-product from both the bromination and conversion steps in this process is hydrogen bromide. Before the hydrocarbons produced in this bromine-based process may be recovered as a liquid product, the hydrogen bromide may need to be separated from the hydrocarbons. The bromine may then be recovered from the hydrogen bromide and recycled within the process. In one instance, an aqueous technique may be used that includes scrubbing the hydrogen bromide from the hydrocarbon stream with an aqueous stream followed by neutralization of the dissolved hydrogen bromide to form a metal bromide salt. The metal bromide salt may then be oxidized to recover the bromine. In another instance, a dry technique may be used that includes reaction of the hydrogen bromide with a metal oxide to form a metal bromide salt, which may then be oxidized to recover the bromine.

SUMMARY

The present invention relates to conversion of gaseous alkanes to liquid hydrocarbons and, more particularly, in one or more embodiments, to a method and system that includes bromination of alkanes followed by conversion of the brominated alkanes to hydrocarbons wherein bromine recovery includes electrolysis.

An embodiment includes a method comprising: providing a stream comprising halogenated alkanes; forming synthesis products comprising hydrocarbons and hydrogen bromide from synthesis reactants comprising at least a portion of the halogenated alkanes; and recovering at least a portion of the bromine, the recovering comprising electrolysis.

Another embodiment includes a method comprising: providing a stream comprising a hydrogen halide; converting at least a portion of the hydrogen halide to at least molecular halogen using gas phase electrolysis; providing a stream comprising hydrocarbons; and forming halogenation products comprising halogenated alkanes and hydrogen halide by reacting at least a portion of the molecular halogen with at least a portion of the hydrocarbons.

Still another embodiment includes a method comprising: providing a stream comprising halogenated alkanes; forming synthesis products comprising hydrocarbons and hydrogen halide from synthesis reactants comprising at least a portion of the halogenated alkanes; separating the at least a portion of the hydrogen halide from the synthesis products; and converting at least a portion of the separated hydrogen halide to at least molecular halogen using liquid phase electrolysis.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 3 is an illustration of an example electrolysis cell that may be used for bromine recovery, in accordance with one embodiment of the present invention.

FIG. 4 is an illustration of another example electrolysis cell that may be used for bromine recovery, in accordance with one embodiment of the present invention.

FIG. 5 is an illustration of yet another example electrolysis cell that may be used for bromine recovery, in accordance with one embodiment of the present invention.

DESCRIPTION OF PREFERRED EMBODIMENTS

The present invention relates to conversion of gaseous alkanes to liquid hydrocarbons and, more particularly, in one or more embodiments, to a method and system that includes bromination of alkanes followed by conversion of the brominated alkanes to hydrocarbons wherein bromine recovery includes electrolysis.

There may be many potential advantages to the methods and systems of the present invention, only some of which are alluded to herein. One of the many potential advantages may be that bromine may be recovered and recycled using electrolysis in a bromine-based process for the production of liquid hydrocarbons. As previously mentioned, hydrogen bromide is generally an undesired byproduct in the bromine-based process for producing liquid hydrocarbons. In accordance with embodiments of the present invention, electric energy may be used to electrolyze the produced hydrogen bromide to form hydrogen and bromine. Accordingly, the bromine may be recovered and recycled within the process.

Figure 1:
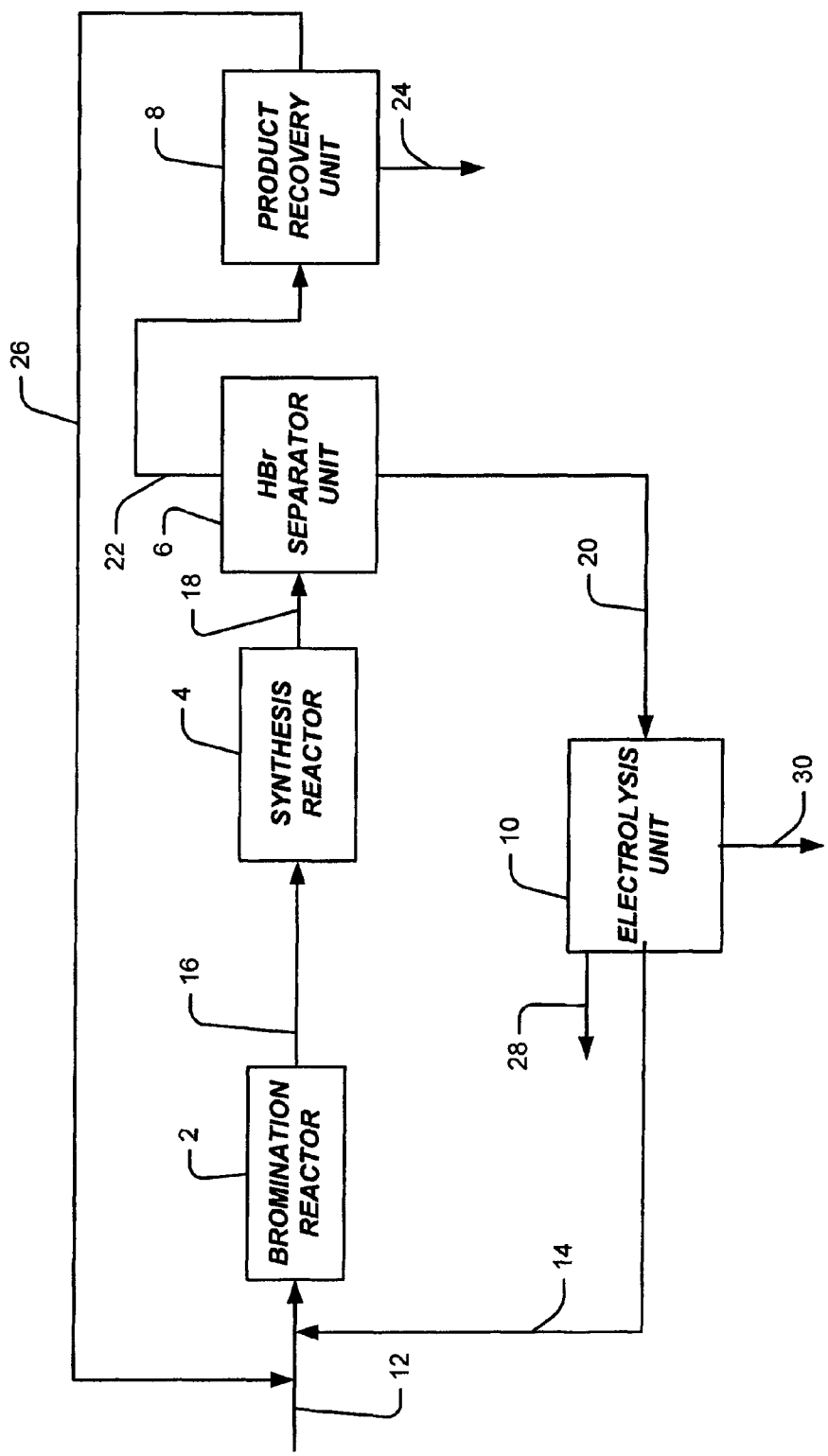
FIG. 1 is an example block diagram of a process for the production of liquid hydrocarbons that includes bromination and uses electrolysis for bromine recovery, in accordance with one embodiment of the present invention.

Referring to FIG. 1, an example block diagram of a process for the production of liquid hydrocarbons that includes liquid-phase electrolysis for bromine recovery is illustrated, in accordance with one embodiment of the present invention. In the illustrated embodiment, the process includes bromination reactor 2, synthesis reactor 4, hydrogen bromide separator unit 6, product recovery unit 8, and liquid-phase electrolysis unit 10. As will be discussed in more detail below, in certain embodiments, liquid-phase electrolysis unit 10 may be used to electrolyze the hydrogen bromide produced in the process, thereby recovering bromine. Accordingly, bromine may be recovered and recycled within the process. In addition, the embodiment of FIG. 1 also may produce hydrogen as a separate product.

As illustrated, gaseous feed stream 12 comprising alkanes may be combined with bromine stream 14, and the resulting mixture may be introduced into bromination reactor 2. While FIG. 1 illustrates the combination of gaseous feed stream 12 and bromine stream 14 prior to bromination reactor 2, those of ordinary skill in the art, with the benefit of this disclosure, should appreciate that gaseous feed stream 12 and bromine stream 14 may be combined in bromination reactor 2. Gaseous feed stream 12 generally comprises alkanes and may be at a pressure, for example, in the range of about 1 atm to about 100 atm and, alternatively, about 1 atm to about 30 atm. The alkanes present in gaseous feed stream 12 may include, for example, lower molecular weight alkanes. As used herein, the term "lower molecular weight alkanes" refers to methane, ethane, propane, butane, pentane, or mixtures thereof. By way of example, the lower molecular weight alkanes present in gaseous feed stream may be methane. Also, gaseous feed stream 12 used in embodiments of the present invention may be any source of gas containing lower molecular weight alkanes whether naturally occurring or synthetically produced. Examples of suitable gaseous feeds that may be used in embodiments of the process of the present invention include, but are not limited to, natural gas, coalbed methane, regasified liquefied natural gas, gas derived from gas hydrates, chlathrates or both, gas derived from anaerobic decomposition of organic matter or biomass, synthetically produced natural gas or alkanes, and mixtures thereof. In certain embodiments, gaseous feed stream 12 may include a feed gas plus a recycled gas stream. In certain embodiments, gaseous feed stream 12 may be treated to remove sulfur compounds and carbon dioxide. In any event, in certain embodiments, small amounts of carbon dioxide, e.g., less than about 2 mol %, may be present in gaseous feed stream 12.

Bromine stream 14 generally comprises bromine and may be at a pressure, for example, in the range of about 1 atm to about 100 atm and, alternatively, of about 1 atm to about 30 atm. In certain embodiments, the bromine may be dry, in that it is substantially free of water vapor. In certain embodiments, the bromine present in bromine stream 14 may be in a gaseous state, a liquid state, or a mixture thereof. As illustrated, bromine stream 14 contains bromine from liquid-phase electrolysis unit 10 that is recovered and recycled within the process. While not illustrated in FIG. 1, additional bromine may also be introduced into the process in the form of a make-up stream. Additionally, while not illustrated, in certain embodiments, the mixture of gaseous feed stream 12 and bromine stream 14 may be passed to a heat exchanger for evaporation of the bromine prior to introduction into bromination reactor 2.

As previously mentioned, gaseous feed stream 12 and bromine stream 14 may be combined and introduced into bromination reactor 2. The mole ratio of the alkanes in gaseous feed stream 12 to the bromine in bromine stream 14 may be, for example, in excess of 2.5:1. While not illustrated, in certain embodiments, bromination reactor 2 may have an inlet pre-heater zone for heating the mixture of the alkanes and bromine to a reaction initiation temperature, for example, in the range of about 250° C. to about 400° C.

In bromination reactor 2, the alkanes may be reacted with the bromine to form brominated alkanes and hydrogen bromide. By way of example, methane may react in bromination reactor 2 with bromine to form brominated methane and hydrogen bromide. In the case of methane reacting with bromine, the formation of mono-brominated methane occurs in accordance with the following general reaction:

$$CH_4 + Br_2 \rightarrow CH_3Br + HBr \qquad (1)$$

This reaction generally occurs with a fairly high selectivity to mono-brominated methane. For instance, in the case of the non-catalyzed bromination of methane operated with excess methane in the range of about 4:1 to about 9:1, the reaction selectivity generally may be in the range of about 70% to about 80% mono-brominated methane and about 20% to about 30% di-brominated methane, on a molar basis. To improve the selectivity with respect to mono-brominated methane, the bromination reaction may be run with a larger excess of methane. In general, it is believed that only very small amounts of tri-brominated methane and tetra-brominated methane should also be formed in the bromination reaction. Higher alkanes, such as ethane, propane, and butane, may also be readily also readily brominated resulting in mono- and multi-brominated alkanes, such as brominated ethane, brominated propane, and brominated butane.

In certain embodiments, the bromination reaction in bromination reactor 2 occurs exothermically, for example, at a temperature in the range of about 250° C. to about 600° C. and at a pressure in the range of about 1 atm to about 100 atm and, alternatively, of about 1 atm to about 30 atm. The upper limit of this temperature range may be greater than the upper limit of the reaction initiation temperature range to which the feed mixture may be heated due to the exothermic nature of the bromination reaction. As will be appreciated by those of ordinary skill in the art, with the benefit of this disclosure, the reaction in bromination reactor 2 may be a homogeneous gas phase reaction or a heterogeneous (catalytic) reaction. Examples of suitable catalysts that may be utilized in bromination reactor 10 include, but are not limited to, platinum, palladium, or supported non-stoichiometric metal oxy-halides such as $FeO_xBr_y$ or $FeO_xCl_y$ or supported stoichiometric metal oxy-halides such as $TaOF_3$, $NbOF_3$, $ZrOF_2$, $SbOF_3$ as described in Olah, et al, J. Am. Chem. Soc. 1985, 107, 7097-7105.

As set forth above, the bromine fed into bromination reactor 2 may be dry, in certain embodiments of the present invention. Elimination of substantially all water vapor from the bromination reaction in bromination reactor 2 should substantially eliminate the formation of unwanted carbon dioxide, thereby increasing the selectivity of the alkane bromination to brominated alkanes and potentially eliminating the large amount of waste heat generated in the formation of carbon dioxide from alkanes. Further, elimination of substantially all water vapor should minimize hydrothermal degradation of downstream catalysts that may be used, in certain embodiments of the present invention.

As illustrated in FIG. 1, brominated stream 16 may be withdrawn from bromination reactor 2 and introduced into synthesis reactor 4. In general, brominated stream 16 withdrawn from bromination reactor 2 comprises brominated alkanes and hydrogen bromide. The brominated alkanes present in brominated stream 16 may comprise mono- and multi-brominated alkanes. While not illustrated at least a portion of brominated stream 16 may be processed to form brominated alkanes with fewer bromine substituents. For example, at least a portion of brominated stream 16 may be treated to convert di-brominated alkanes to mono-brominated alkanes. Examples of this processing may include reaction of the di-brominated alkanes with lower molecular weight alkanes (such as methane, ethane, propane, or butanes) or reaction of the di-brominated alkanes with hydrogen. These reactions may occur, for example, in the presence of a catalyst such as a metal bromide or metal oxy-halide catalyst. While also not illustrated, brominated stream 16 may be cooled in a heat exchanger to a temperature in the range of about 150° C. to about 450° C. before being introduced to synthesis reactor 4.

In synthesis reactor 4, the brominated alkanes may be reacted exothermically in the presence of a catalyst to form product hydrocarbons and additional hydrogen bromide. The reaction may occur, for example, at a temperature in the range of about 150° C. to about 500° C. and a pressure in the range of about 1 atm to 100 atm and, alternatively of about 1 atm to about 30 atm. The product hydrocarbons generally may include, for example, C3, C4, and C5+ gasoline-range and heavier hydrocarbon, including, for example, alkanes and aromatics, as well as olefins, such as ethylene, propylene, and the like. Example processes for the production of product hydrocarbons that include bromination followed by a synthesis reaction are described in more detail in U.S. Pat. No. 7,244,867, U.S. Pat. No. 7,348,464, and U.S. Patent Pub. No. 2006/0100469, the entire disclosures of which incorporated herein by reference.

The catalyst may be any of a variety of suitable materials for catalyzing the conversion of the brominated alkanes to higher molecular weight hydrocarbons. In certain embodiments, synthesis reactor 4 may comprise a fixed bed of the catalyst. A fluidized-bed of synthesis catalyst may also be used in certain circumstances, particularly in larger applications and may have certain advantages, such as constant removal of coke and a steady selectivity to product composition. Examples of suitable catalysts include a fairly wide range of materials that have the common functionality of being acidic ion-exchangers and which also contain a synthetic crystalline alumino-silicate oxide framework. In certain embodiments, a portion of the aluminum in the crystalline alumino-silicate oxide framework may be substituted with magnesium, boron, gallium and/or titanium. In certain embodiments, a portion of the silicon in the crystalline alumino-silicate oxide framework may be optionally substituted with phosphorus. The crystalline alumino-silicate catalyst generally may have a significant anionic charge within the crystalline alumino-silicate oxide framework structure which may be balanced, for example, by cations of elements selected from the group H, Li, Na, K or Cs or the group Mg, Ca, Sr or Ba. Although zeolitic catalysts may be commonly obtained in a sodium form, a protonic or hydrogen form (via ion-exchange with ammonium hydroxide, and subsequent calcining) is preferred, or a mixed protonic/sodium form may also be used. The zeolite may also be modified by ion exchange with other alkali metal cations, such as Li, K, or Cs, with alkali-earth metal cations, such as Mg, Ca, Sr, or Ba, or with transition metal cations, such as Ni, Cu, Fe, Mn, V, and W or with rare-earth metal cations such as La or Ce. Such subsequent ion-exchange, may replace the charge-balancing counter-ions, but furthermore may also partially replace ions in the oxide framework resulting in a modification of the crystalline make-up and structure of the oxide framework. The crystalline alumino-silicate or substituted crystalline alumino-silicate may include a microporous or mesoporous crystalline aluminosilicate, but, in certain embodiments, may include a synthetic microporous crystalline zeolite, and, for example, being of the MFI structure such as ZSM-5. Moreover, the crystalline alumino-silicate or substituted crystalline alumino-silicate, in certain embodiments, may be subsequently impregnated with an aqueous solution of a Mg, Ca, Sr, or Ba, La or Ce salt. In certain embodiments, the salts may be a halide salt, such as a bromide salt, such as $MgBr_2$ or $CeBr_3$. Optionally, the crystalline alumino-silicate or substituted crystalline alumino-silicate may also contain between about 0.1 to about 1 weight % Pt, about 0.1 to 5 weight % Pd, or about 0.1 to about 5 weight % Ni in the metallic state. Although, such materials are primarily initially crystalline, it should be noted that some crystalline catalysts may undergo some loss of crystallinity either due to initial ion-exchange or impregnation or due to operation at the reaction conditions or during regeneration and hence may also contain significant amorphous character, yet still retain significant, and in some cases improved activity.

The particular catalyst used in synthesis reactor 4 will depend, for example, upon the particular product hydrocarbons that are desired. For example, when product hydrocarbons having primarily C3, C4 and C5+ gasoline-range aromatic compounds and heavier hydrocarbon fractions are desired, a ZSM-5 zeolite catalyst may be used. When it is desired to produce product hydrocarbons comprising a mixture of olefins and $C_5+$ products, an X-type or Y-type zeolite catalyst or SAPO zeolite catalyst may be used. Examples of suitable zeolites include an X-type, such as 10-X, or Y-type zeolite, although other zeolites with differing pore sizes and acidities, may be used in embodiments of the present invention.

The temperature at which synthesis reactor 4 is operated is one parameter in determining the selectivity of the reaction to the particular product hydrocarbons desired. Where, for example, an X-type or Y-type zeolite or SAPO zeolite catalyst is used and it is desired to produce olefins, synthesis reactor 4 may be operated at a temperature within the range of about 250° C. to about 500° C. Temperatures above about 450° C. in synthesis reactor 4 may result in increased yields of light hydrocarbons, such as undesirable methane and also deposition of coke, whereas lower temperatures generally should increase yields of ethylene, propylene, butylene and heavier molecular weight hydrocarbons. In the case of the alkyl bromide reaction over the 10 X zeolite catalyst, for example, it is believed that cyclization reactions also may occur such that the C7+ fractions contain substantial substituted aromatics. At increasing temperatures approaching about 400° C., for example, it is believed that brominated methane conversion generally should increase towards about 90% or greater; however, selectivity towards $C_5+$ hydrocarbons generally should decrease with increased selectivity toward lighter products, such as olefins. At temperatures exceeding about 550° C., for example, it is believed that a high conversion of brominated methane to methane and carbonaceous coke occurs. In the temperature range of between about 300° C. and about 450° C., as a byproduct of the reaction, a lesser amount of coke probably will build up on the catalyst over time during operation, causing a decline in catalyst activity over a range of hours, up to hundreds of hours, depending on the reaction conditions and the composition of the feed gas. Conversely, temperatures at the lower end of the range (e.g., below about 300° C.), may also contribute to coking due to a reduced rate of desorption of heavier products from the catalyst. Hence, operating temperatures within the range of about 250° C. to about 500° C., but preferably in the range of about 350° C. to about 450° C. in synthesis reactor 4 should generally balance increased selectivity of the desired olefins and $C_5+$ hydrocarbons and lower rates of deactivation due to carbon formation, against higher conversion per pass, which should minimize the quantity of catalyst, recycle rates and equipment size required.

Where, for example, the product hydrocarbons desired are primarily C3, C4, and C5+ gasoline-range and heavier hydrocarbon fractions, synthesis reactor 4 may be operated at a temperature within the range of about 150° C. to about 450° C. Temperatures above about 300° C. in synthesis reactor 4 may result in increased yields of light hydrocarbons, whereas lower temperatures generally may increase yields of heavier molecular weight hydrocarbons. By way of example, at the low end of the temperature range with brominated methane reacting over the ZSM-5 zeolite catalyst at temperatures as low as about 150° C., significant brominated methane conversion on the order of about 20% may occur, with a high selectivity towards $C_5+$ hydrocarbons. In the case of the brominated methane reaction over the ZSM-5 zeolite catalyst, for example, cyclization reactions also occur such that the C7+ fractions may be primarily comprise substituted aromatics. At increasing temperatures approaching about 300° C., for example, brominated methane conversion generally should increase towards about 90% or greater; however, selectivity towards $C_5+$ hydrocarbons generally may decrease and selectivity towards lighter products, particularly undesirable methane, may increase. Surprisingly, benzene, ethane or $C_2$-$C_3$ olefin components are not typically present, or present in only very small quantities, in the reaction effluent, in accordance with certain embodiments, such as when a ZSM-5 catalyst is used at temperatures of about 390° C. However, at temperatures approaching about 450° C., for example, almost complete conversion of brominated methane to methane and carbonaceous coke may occur. In the operating temperature range of between about 350° C. and about 420° C., as a byproduct of the reaction, a small amount of carbon may build up on the catalyst over time during operation, potentially causing a decline in catalyst activity over a range of hours, up to several days, depending on the reaction conditions and the composition of the feed gas. It is believed that higher reaction temperatures (e.g., above about 420° C.), associated with the formation of methane, favor the thermal cracking of brominated alkanes and formation of carbon or coke and hence an increase in the rate of deactivation of the catalyst. Conversely, temperatures at the lower end of the range (e.g., below about 350° C.) may also contribute to coking due to a reduced rate of desorption of heavier products from the catalyst. Hence, operating temperatures within the range of about 150° C. to about 450° C., but preferably in the range of about 350° C. to about 420° C., and most preferably, in the range of about 370° C. to about 400° C., in synthesis reactor 4 should generally balance increased selectivity of the desired $C_5+$ hydrocarbons and lower rates of deactivation due to carbon formation, against higher conversion per pass, which minimizes the quantity of catalyst, recycle rates and equipment size required.

The catalyst may be periodically regenerated in situ, by isolating synthesis reactor 4 from the normal process flow and purging with an inert gas, for example, at a pressure in a range of about 1 atm to about 5 atm bar at an elevated temperature in the range of about 400° C. to about 650° C. to remove unreacted material adsorbed on the catalyst insofar as is practical. Then, the deposited heavy products, coke, or both may be oxidized to $CO_2$, CO, and $H_2O$ by addition of air or inert gas-diluted oxygen to synthesis reactor 4, for example, at a pressure in the range of about 1 atm to about 5 atm at an elevated temperature in the range of about 400° C. to about 650° C. The oxidation products and residual air or inert gas may be vented from synthesis reactor 4 during the regeneration period. However, as the regeneration off-gas may contain small amounts of bromine-containing species, as well as excess unreacted oxygen, the regeneration gas effluent may be directed into the oxidation portion of the process, wherein the bromine-containing species may be converted to elemental bromine and recovered for re-use within the process.

As illustrated in FIG. 1, synthesis outlet stream 18 may be withdrawn from synthesis reactor 4. In general, synthesis outlet stream 18 may comprise product hydrocarbons and the additional hydrogen bromide generated in synthesis reactor 4. Synthesis outlet stream 18 further may comprise the hydrogen bromide generated in bromination reactor 2. For example, synthesis outlet stream 18 may include C3, C4, and C5+ gasoline-range and heavier hydrocarbons, including, for example, alkanes and aromatics, as well as olefins, such as ethylene, propylene, and the like. By way of further example, synthesis outlet stream 18 may comprise C3, C4 and C5+ gasoline-range and heavier hydrocarbon fractions, as well as the additional hydrogen bromide. In certain embodiments, the C7+ fraction of the hydrocarbons present in synthesis outlet stream 18 may primarily comprise substituted aromatics.

As set forth above, the process of FIG. 1 further includes hydrogen bromide separator unit 6. In the illustrated embodiment, synthesis outlet stream 18 may be introduced to hydrogen bromide separator unit 6. In hydrogen bromide separator unit 6, at least a portion of the hydrogen bromide present in synthesis outlet stream 18 may be separated from the product hydrocarbons. In certain embodiments, greater than about 98%, and up to nearly 100% of the hydrogen bromide may be separated from the product hydrocarbons. An example of a suitable process for use in hydrogen bromide separator unit 6 may include contacting synthesis outlet stream 18, which may be a gas, with a liquid. Hydrogen bromide present in synthesis outlet stream 18 may be dissolved in the liquid and the mixture may be removed from hydrogen bromide separator unit 6 via electrolysis feed stream 20. As described in more detail below, hydrocarbon stream 22 that may comprise the product hydrocarbons may be removed from hydrogen bromide separator unit 6.

One example of a suitable liquid that may be used to scrub the hydrogen bromide from the product hydrocarbons includes water. In these embodiments, the hydrogen bromide dissolves into the water and is at least partially ionized, forming an aqueous acid solution. Another example of a suitable liquid that may be used to scrub the hydrogen bromide from the product hydrocarbons includes an aqueous partially oxidized metal bromide salt solution containing metal hydroxide species, metal oxy-bromide species, metal oxide species, or mixtures thereof. The hydrogen bromide dissolved in the partially oxidized metal bromide salt solution should be neutralized to form metal bromide salt in electrolysis feed stream 20 that may be removed from hydrogen bromide separator unit 6. Examples of suitable metals of the bromide salt include $Fe(III)$, $Cu(II)$, and $Zn(II)$, as these metals may be less expensive and may be oxidized at lower temperatures, for example, in the range of about 120° C. to about 200° C. However, other metals that form oxidizable bromide salts may also be used. In certain embodiments, alkaline earth metals which may also form bromide salts and hydroxides, such as Ca(II) or Mg(II) may be used.

As noted above, hydrocarbon stream 22 comprising the product hydrocarbons may be removed from hydrogen bromide separator unit 6. In general, hydrocarbon stream 22 comprises the excess unreacted alkanes and the product hydrocarbons from which the hydrogen bromide was separated. As illustrated in FIG. 1, hydrocarbon stream 22 may be introduced to product recovery unit 8 to recover, for example, the C5+ hydrocarbons as liquid product stream 24. Liquid product stream 24 may comprise, for example, C5+ hydrocarbons, including alkanes and substituted aromatics. In certain embodiments, liquid product stream 24 may comprise olefins, such as ethylene, propylene, and the like. In certain embodiments, liquid product stream 24 may comprise various hydrocarbons in the liquefied petroleum gas and gasoline-fuels range, which may include a substantial aromatic content, significantly increasing the octane value of the hydrocarbons in the gasoline-fuels range. While not illustrated, in certain embodiments, product recovery unit 8 may include dehydration and liquids recovery. Any conventional method of dehydration and liquids recovery, such as solid-bed dessicant adsorption followed by refrigerated condensation, cryogenic expansion, or circulating absorption oil or other solvent, as used to process natural gas or refinery gas streams, and to recover product hydrocarbons, may be employed in embodiments of the present invention.

At least a portion of the residual vapor effluent from product recovery unit 8 may be recovered as alkane recycle stream 26. Alkane recycle stream 26 may comprise, for example, methane and possibly other unreacted lower molecular weight alkanes. As illustrated, alkane recycle stream 26 may be recycled and combined with gaseous feed stream 12. In certain embodiments, alkane recycle stream 26 that is recycled may be at least 1.5 times the feed gas molar volume. While not illustrated in FIG. 1, in certain embodiments, another portion of the residual vapor effluent from product recovery unit 8 may be used as fuel for the process. Additionally, while also not illustrated in FIG. 1, in certain embodiments, another portion of the residual vapor effluent from product recovery unit 8 may be recycled and used to dilute the brominated alkane concentration introduced into synthesis reactor 4. Where used to dilute the brominated alkane concentration, the residual vapor effluent generally should be recycled at a rate to absorb the heat of reaction such that synthesis reactor 4 is maintained at the selected operating temperature, for example, in the range of about 150° C. to about 500° C. in order to maximize conversion versus selectivity and to minimize the rate of catalyst deactivation due to the deposition of carbonaceous coke. Thus, the dilution provided by the recycled vapor effluent should permit selectivity of bromination in bromination reactor 2 to be controlled in addition to moderating the temperature in synthesis reactor 4.

As set forth above, the hydrogen bromide may be separated from the product hydrocarbons in hydrogen bromide separator unit 6. As illustrated in FIG. 1, electrolysis feed stream 20 may be withdrawn from hydrogen bromide separator unit 6 and supplied to liquid-phase electrolysis unit 10. In certain embodiments, electrolysis feed stream 20 may contain water and the separated hydrogen bromide dissolved therein. In certain embodiments, electrolysis feed stream 20 may contain water and the neutralized hydrogen bromide in the form of a metal bromide salt dissolved therein. The metal bromide salt may be present in electrolysis feed stream 20, for example, in the embodiments wherein the hydrogen bromide is neutralized in the liquid used to scrub the hydrogen bromide from the product hydrocarbons.

In liquid-phase electrolysis unit 10, bromine may be recovered from the hydrogen bromide or the metal bromide salt present in electrolysis feed stream 20. Electric energy may be used, in the hydrogen bromide electrolysis embodiments, to electrolyze at least a portion of the hydrogen bromide to form elemental bromine and hydrogen and, in the metal bromide salt electrolysis embodiments, to electrolyze at least a portion of the metal bromide to form the elemental bromine and the metal, metal ion in the reduced state or metal hydroxide. The presence of a reducible metal ion in solution may have the advantage of reducing the cathodic overpotential required, hence minimizing power requirements as compared to the electrolysis of aqueous acid. In the electrolysis of an aqueous hydrochloric acid solution (HCl), the Uhde process may be used and may also possibly be adapted for the electrolysis of the aqueous hydrobromic acid, e.g., the hydrogen bromide dissolved in electrolysis feed stream 20.

While not illustrated in FIG. 1, one or more electrolysis cells may be included in liquid phase electrolysis unit 10. Those of ordinary skill in the art, with the benefit of this disclosure, will appreciate that the electrolysis cells may be operated in parallel or series, in accordance with certain embodiments of the present invention. In the electrolysis of hydrogen bromide embodiments, electric energy may be passed through electrolysis feed stream 20 that comprises water and hydrogen bromide dissolved therein with the production of bromine at the anode and hydrogen at the cathode of the electrolysis cells. In the electrolysis of the metal bromide salt, electric energy may be passed through electrolysis feed stream 20 that comprises water and the metal bromide salt dissolved therein with the production of bromine at the anode and the metal, metal ion in the reduce state or metal hydroxide at the cathode of the electrolysis cells. While not illustrated, the energy required to separate the hydrogen and the bromine may be provided by an electrical power supply.

By way of example, the electrolysis of hydrogen bromide may occur in an aqueous hydrobromic acid solution in the substantial absence of a metal ion, in accordance with the following general half-reactions occurring at the anode and cathode electrodes, respectively, of the electrolysis cells:

$$2Br(-) \rightarrow Br_2 + 2e^- \quad (2)$$

$$2H(+) + 2e^- \rightarrow H_2 \quad (3)$$

By way of further example, the electrolysis of a metal bromide salt (e.g., Fe(III)Br$_3$) may occur in accordance with the following general half-reactions occurring at the anode and cathode electrodes, respectively, of the electrolysis cells:

$$2Br(-) \rightarrow Br_2 + 2e^- \quad (4)$$

$$2Fe(+3) + 2e^- \rightarrow 2Fe(+2) \quad (5)$$

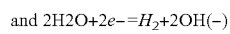
and $2H_2O + 2e^- = H_2 + 2OH(-)$

Where Fe(+3) and Fe(+2) may further react with OH(−) to form iron hydroxides.

Accordingly, bromine may be generated in liquid-phase electrolysis unit 10, in accordance with embodiments of the present invention. Bromine stream 14 comprising the bromine may be removed from liquid-phase electrolysis unit 10 and supplied to bromination reactor 2. Accordingly, bromide may be recovered and recycled within the process, in accordance with embodiments of the present invention. Furthermore, dependent upon whether hydrogen bromide, a metal bromide salt, or both is supplied to liquid-phase electrolysis unit, a reduced metal ion, hydroxyl ion, or metal hydroxide, a hydrogen, or two or more of these should also be generated in liquid-phase electrolysis unit 10. Accordingly, hydrogen/reduced metal ion stream 28 comprising the hydrogen, the reduced metal ion, hydroxyl ion or metal hydroxide, or two or more of these may also be removed from liquid-phase electrolysis unit 10. Among other uses, the hydrogen may be recycled within the process or used in additional processes, such as petroleum refining or chemical synthesis. Furthermore, water stream 30 comprising the water in which the hydrogen bromide (or metal bromide salt) is electrolyzed may also be removed from liquid-phase electrolysis unit 10.

In one embodiment, one or more of the electrolysis cells in liquid-phase electrolysis unit 10 may be operated in an air-depolarized mode in which air is passed over the cathode. In the air-depolarized mode embodiments, hydrogen bromide electrolysis should produce water at the cathode and metal bromide salt electrolysis should produce a metal hydroxide or metal oxide at the cathode. By way of example, the electrolysis of hydrogen bromide in air-depolarized mode embodiments may produce water at the cathode and partially depolarize the electrode according to the following reaction:

$$2H(+) + \frac{1}{2}O_2 + 2e^- \rightarrow H_2O \qquad (6)$$

The air-depolarized embodiments may be particularly useful where there is no local need for hydrogen. In certain embodiments, two or more electrolysis cells may be used in parallel with one or more operated with an air-depolarized cathode producing water rather than hydrogen.

By way of further example, the electrolysis of a metal bromide salt (e.g., Fe(III)Br$_3$) in air-depolarized mode embodiments may produce free hydroxide and partially depolarize the electrode according to the following overall reaction:

Figure 2:
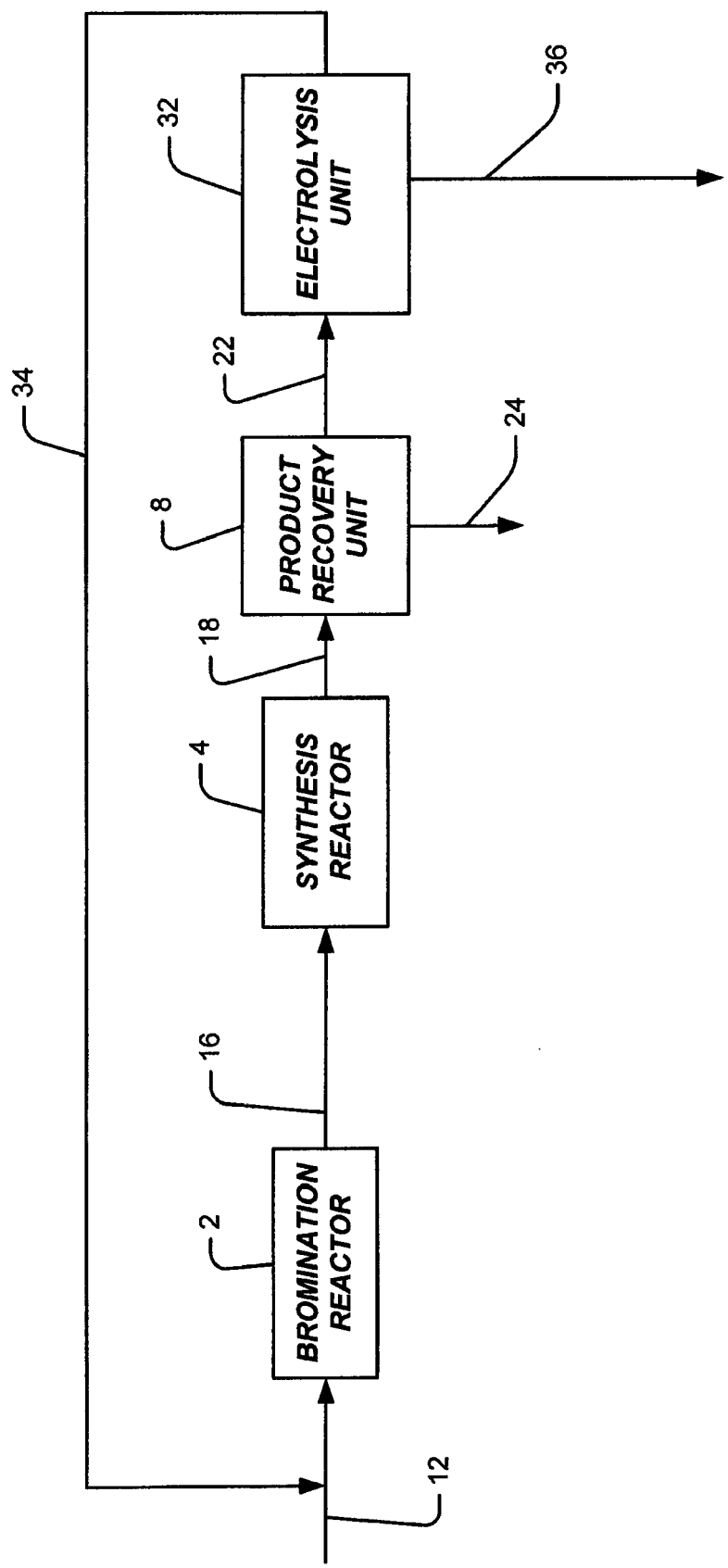
FIG. 2 is an example block diagram of another process for the production of liquid hydrocarbons that includes bromination and uses electrolysis for bromine recovery, in accordance with one embodiment of the present invention.

Referring to FIG. 2, an example block diagram of a process for the production of product hydrocarbons that includes vapor-phase electrolysis for bromine recovery is illustrated, in accordance with one embodiment of the present invention. In the illustrated embodiment, the process includes bromination reactor 2, synthesis reactor 4, product recovery unit 8, and vapor-phase electrolysis unit 32. As will be discussed in more detail below, in certain embodiments, vapor-phase electrolysis unit 32 may be used to electrolyze the hydrogen bromide produced in the process, thereby recovering bromine. Accordingly, bromine may be recovered and recycled within the process.

As illustrated in FIG. 2, gaseous feed stream 12 comprising alkanes may be combined with recycle stream 34 and the resulting mixture may be introduced into bromination reactor 2. As will be discussed in more detail below, recycle stream 34 may comprise unreacted lower molecular weight alkanes and recovered bromine from vapor-phase electrolysis unit 32. While not illustrated, additional bromine may also be introduced into the process in the form of a make-up stream. In bromination reactor 2, the alkanes may be reacted with the bromine to form brominated alkanes and hydrogen bromide. Brominated stream 16 may be withdrawn from bromination reactor 2 and supplied to synthesis reactor 4. In general, brominated stream 16 withdrawn from bromination reactor 2 comprises halogenated alkanes and hydrogen halide. In synthesis reactor 4, the brominated alkanes may be reacted exothermically in the presence of a catalyst to form product hydrocarbons and additional hydrogen bromide. Synthesis outlet stream 18 may be withdrawn from synthesis reactor 4. In general, synthesis outlet stream 18 may comprise product hydrocarbons and the additional hydrogen bromide generated in synthesis reactor 4. Synthesis outlet stream 18 further may comprise the hydrogen bromide generated in bromination reactor 2.

In the illustrated embodiment, synthesis outlet stream 18 may be introduced to product recovery unit 8 to recover, for example, the product hydrocarbons as liquid product stream 24. Liquid product stream 24 may comprise, for example, C5+ hydrocarbons, including alkanes and substituted aromatics. In certain embodiments, liquid product stream 32 may comprise olefins, such as ethylene, propylene, and the like. In certain embodiments, liquid product stream 24 may comprise various hydrocarbons in the liquefied petroleum gas and gasoline-fuels range, which may include a substantial aromatic content, significantly increasing the octane value of the hydrocarbons in the gasoline-fuels range.

Vapor effluent stream 22 from product recovery unit 8 may be supplied to vapor-phase electrolysis unit 32. In certain embodiments, vapor effluent stream 22 may comprise methane and possibly other unreacted lower molecular weight alkanes. In addition, in the embodiment illustrated in FIG. 2, vapor effluent stream 22 further may comprise hydrogen bromide that was present in synthesis outlet stream 30 that was introduced to product recovery unit 8. This hydrogen bromide may have been generated in bromination reactor 2 and synthesis reactor 4.

In vapor-phase electrolysis unit 32, bromine may be recovered from the hydrogen bromide present in vapor effluent stream 22. Electric energy may be used to electrolyze at least a portion of the hydrogen bromide to form elemental bromine and hydrogen. The electrolysis of hydrogen bromide may generally occur in accordance with the half-reactions illustrated previously in equations (2) and (3). An example process for the vapor-phase electrolysis of hydrogen bromide is described in U.S. Pat. No. 5,411,641, the entire disclosure of which is incorporated herein by reference. While not illustrated in FIG. 2, one or more electrolysis cells may be included in vapor-phase electrolysis unit 32. In certain embodiments, one or more of the electrolysis cells in vapor-phase electrolysis unit 32 may be operated in an air-depolarized mode in which air is passed over the cathode. In the air-depolarized mode embodiments, hydrogen bromide electrolysis should produce water at the cathode in accordance with the half-reaction illustrated by equation (6) above. The air-depolarized embodiments may be particularly useful where there is no local need for hydrogen. In certain embodiments, two or more electrolysis cells may be used in parallel with one or more operated with an air-depolarized cathode producing water rather than hydrogen.

Accordingly, bromine may be recovered in vapor-phase electrolysis unit 32, in accordance with embodiments of the present invention. Recycle stream 34 may be removed from vapor-phase electrolysis unit 32. Recycle stream 34 may comprise, for example, the recovered bromine as well as methane and potentially other unreacted lower molecular weight alkanes that were not recovered in product recovery unit 8. As illustrated recycled stream 34 may be recycled and combined with gaseous feed stream 12. In certain embodiments, recycle stream 34 that is recycled may contain alkanes in an amount that is at least 1.5 times the feed gas molar volume. While not illustrated in FIG. 1, in certain embodiments, another portion of recycle stream 34 may be used as fuel for the process. Additionally, while also not illustrated in FIG. 1, in certain embodiments, another portion of recycle stream 34 may be recycled and used to dilute the brominated alkane concentration introduced into synthesis reactor 4. Where used to dilute the brominated alkane concentration, the portion of recycle stream 34 generally should be recycled at a rate to absorb the heat of reaction such that synthesis reactor 4 is maintained at the selected operating temperature, for example, in the range of about 150° C. to about 500° C. in order to maximize conversion versus selectivity and to minimize the rate of catalyst deactivation due to the deposition of carbonaceous coke. Thus, the dilution provided by the recycled vapor effluent should permit selectivity of bromination in bromination reactor 2 to be controlled in addition to moderating the temperature in synthesis reactor 4.

As noted above, hydrogen also should be produced in vapor-phase electrolysis unit 32. Accordingly, hydrogen stream 36 comprising the hydrogen may also be removed from vapor-phase electrolysis unit 32. Among other uses, the hydrogen may be recycled within the process or used in additional processes, such as petroleum refining or chemical synthesis. In certain embodiments, if one or more cells of vapor-phase electrolysis unit 32 are operating in an air-depolarized mode, the produced water also may be removed from vapor-phase electrolysis unit 32.

As set forth above with respect to FIGS. 1 and 2, liquid-phase electrolysis unit 10 and vapor-phase electrolysis unit 32 may be used to recover bromine from hydrogen bromide, metal bromide salts, or a combination thereof, in accordance with embodiments of the present invention. Those of ordinary skill in the art, with the benefit of this disclosure, will recognize that a variety of different electrochemical cells, and arrangements thereof, may be used in accordance with embodiments of the present invention for the vapor-phase or liquid-phase electrolysis of hydrogen bromide. FIGS. 3-5 illustrate electrolysis cells that may be used in accordance with embodiments of the present invention.

Referring to FIG. 3, an example electrolysis cell that may be used for bromine recovery is illustrated, in accordance with one embodiment of the present invention. In the illustrated embodiment, electrolysis cell 38 includes anode side 40, cathode side 42, and cation-transporting membrane 44, wherein anode side 40 and cathode side 42 are each disposed on opposite sides of cation-transporting membrane 44. Examples of suitable cation-transporting membranes include a cationic membrane that comprise fluoro or perfluoromonomers, such as a copolymer of two or more fluoro or perfluoromonomers at least one of which contains pendant sulfonic acid groups. Another example of a suitable cation-transporting membrane includes proton-conducting ceramics, such as beta-alumina. In the illustrated embodiment, feed stream 46 comprising, for example, hydrogen bromide, may be introduced through an inlet of electrolysis cell 38 on anode side 40 of cation-transporting membrane 44. In electrolysis cell 38, electric energy may be used to reduce molecules of the hydrogen bromide to produce bromide anions and hydrogen cations. The bromide anions may form bromine on the anode side 40 of electrolysis cell 38. As illustrated, the hydrogen cations may be transported through cation-transporting membrane 44 to cathode side 42 where the hydrogen cations may combine with electrons to form hydrogen gas. Hydrogen stream 48 and bromine stream 50 may be withdrawn from electrolysis cell 38.

Referring to FIG. 4, another example of electrolysis cell 38 that may be used for bromine recovery is illustrated, in accordance with one embodiment of the present invention. In the illustrated embodiment, electrolysis cell 38 is operated in an air-depolarized mode. As illustrated, oxygen stream 50 may be introduced into cathode side 42 of cation-transporting membrane 44, such that the oxygen combines with the hydrogen cations in accordance with the half-reaction illustrated by equation (6) above to form water, which may be withdrawn from electrolysis cell 38 via water stream 52.

Referring to FIG. 5, another example electrolysis cell that may be used for bromine recovery is illustrated, in accordance with one embodiment of the present invention. In the illustrated embodiment, alternative electrolysis cell 54 includes anode side 56, cathode side 58, and anion-transporting membrane 60, wherein anode side 56 and cathode side 58 are each disposed on opposite sides of anion-transporting membrane 60. An example of a suitable anion-transporting membrane includes a molten-salt saturated membrane. In the illustrated embodiment, feed stream 46 comprising, for example, hydrogen bromide, may be introduced through an inlet of alternative electrolysis cell 54 on cathode side 58 of anion-transporting membrane 60. In alternative electrolysis cell 54, electric energy may be used to reduce molecules of the hydrogen bromide to produce bromide anions and hydrogen cations. On the cathode side 58, the hydrogen cations may combine with electrons to form hydrogen. As illustrated, the bromide anions may be transported through anion-transporting membrane 60 to anode side 56 where the bromide anions may combine yielding electrons and forming bromine. Hydrogen stream 48 and bromine stream 50 may be withdrawn from alternative electrolysis cell 54.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified, and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Moreover, the indefinite articles "a" or "an", as used in the claims, are defined herein to mean one or more than one of the element that it introduces. Also, the terms in the claims have their plain, ordinary meaning unless otherwise explicitly and clearly defined by the patentee.

What is claimed is:

1. A method comprising:
   providing a stream comprising halogenated alkanes;
   forming synthesis products comprising hydrocarbons and hydrogen bromide from synthesis reactants comprising at least a portion of the halogenated alkanes;
   separating the synthesis products into at least a liquid product stream comprising C5+ hydrocarbons and a vapor stream comprising hydrogen bromide and methane; and
   recovering bromine from the hydrogen bromide in an electrolysis unit.

2. The method of claim 1 further comprising:
   forming the halogenated alkanes by reacting an alkane stream and a halogen stream.

3. The method of claim 2 wherein the alkane stream may be at a pressure in the range of about 1 atm to about 100 atm.

4. The method of claim 2 wherein the alkane stream comprise at least one alkane selected from the group consisting of:

methane, ethane, propane, butane, pentane, natural gas, coalbed methane, regasified liquefied natural gas, gas derived from gas hydrates, gas derived from chlathrates, gas derived from anaerobic decomposition of organic matter, gas derived from anaerobic decomposition of biomass, or synthetically produced alkanes.

5. The method of claim 2 wherein the forming of the halogenated alkanes occurs in the presence of a catalyst.

6. The method of claim 1 wherein the forming synthesis products occurs at a temperature in the range of about 150° C. to about 500° C. and at a pressure in the range of about 1 atm to 100 atm.

7. The method of claim 1 wherein the electrolysis unit comprises an electrolysis cell, wherein the electrolysis cell comprises an anode side, a cathode side, and a ion-transporting membrane, wherein the anode side and the cathode side are each disposed on opposite sides of the ion-transporting membrane.

8. The method of claim 7 wherein the ion-transporting membrane comprises a cation-transporting membrane, wherein the cation-transporting membrane comprises at least one material selected from the group consisting of: a fluoromonomer, perfluoromonomer, a copolymer of two or more fluoro or perfluoromonomers at least one of which contains pendant sulfonic acid groups, a proton-conducting ceramic, or a derivative thereof.

9. The method of claim 1 wherein hydrogen is formed in the electrolysis unit.

10. The method of claim 1 wherein the forming synthesis products occurs in the presence of a catalyst.

11. The method of claim 10 wherein the catalyst comprises a synthetic crystalline alumino-silicate catalyst.

12. A method comprising:
forming synthesis products comprising hydrocarbons and hydrogen bromide from synthesis reactants comprising brominated alkanes;
separating the synthesis products into at least a liquid product stream comprising C5+ hydrocarbons and a vapor stream comprising hydrogen bromide and methane; and
converting at least a portion of the hydrogen bromide to at least molecular bromine using as phase electrolysis;
providing a stream comprising hydrocarbons; and
forming bromination products by reacting at least a portion of the molecular bromine with at least a portion of the hydrocarbons.

13. The method of claim 12 wherein the forming of the bromination products occurs at a temperature in the range of about 250° C. to about 600° C. and at a pressure in the range of about 1 atm to about 100 atm.

14. The method of claim 12 wherein the forming of the bromination products occurs in the presence of a catalyst.

15. The method of claim 14 wherein the catalyst comprises at least one catalytic material selected from the group consisting of platinum, palladium, unsupported oxy halides of the formula $FeO_xBr_y$, unsupported oxy halides of the formula $FeO_xCl_y$, $TaOF_3$, $NbOF_3$, $ZrOF_2$, $SbOF_3$.

16. The method of claim 12 wherein the electrolysis occurs in an electrolysis cell operated in an air-depolarized mode.

17. The method of claim 12 wherein hydrogen is formed in the gas phase electrolysis.

18. The method of claim 12 wherein the forming synthesis products occurs in the presence of a catalyst.

19. The method of claim 18 wherein the catalyst comprises a synthetic crystalline alumino-silicate catalyst.

20. A method comprising:
reacting at least a gaseous feed stream comprising lower molecular weight hydrocarbons with bromine in a bromination reactor to form at least hydrogen bromide and brominated alkanes;
reacting at least a portion of the brominated alkanes in the presence of synthetic crystalline alumino-silicate catalyst in a synthesis reactor to form at least product hydrocarbons comprising hydrocarbons having three or more carbons and additional hydrogen bromide;
feeding at least a portion of the product hydrocarbons and the additional hydrogen bromide from the synthesis reactor to a product recovery unit;
recovering a liquid product stream from the product recovery unit, the liquid product stream comprising hydrocarbons having five or more hydrocarbons;
recovering a vapor stream from the product recovery unit, the vapor stream comprising hydrogen bromide; and
converting at least a portion of the hydrogen bromide from the vapor stream to at least molecular bromine using a gas phase electrolysis unit.

21. The method of claim 20 further comprising recycling at least methane from the product recovery unit to the bromination reactor.

22. The method of claim 20 wherein the lower molecular weight alkanes comprise methane.

23. The method of claim 20 wherein the lower molecular weight alkanes comprise at least one gaseous feed selected from the group consisting of natural gas, coalbed methane, regasified liquefied natural gas, gas derived from gas hydrates, gas derived from chlathrates, gas derived from anaerobic decomposition of organic matter, gas derived from anaerobic decomposition of biomass, synthetically produced natural gas, synthetically produced alkanes, and any combinations thereof.

24. The method of claim 20 wherein the brominated alkanes comprise monobrominated alkanes.

25. The method of claim 20 wherein a mole ratio of lower molecular weight alkanes to the bromine in the gaseous feed is in excess of 2.5:1.

26. The method of claim 20 wherein the synthetic crystalline alumino-silicate comprises a ZSM-5 zeolite catalyst.

27. The method of claim 20 wherein the gas phase electrolysis unit comprises an electrolysis cell operated in an air-depolarized mode.

28. The method of claim 27 further comprising recovering water from the phase electrolysis unit.

29. The method of claim 20 further comprising recovering hydrogen from the gas phase electrolysis unit.

30. The method of claim 20 wherein the liquid product stream comprises C5+ gasoline-range hydrocarbons.

* * * * *